(12) United States Patent
Banet et al.

(10) Patent No.: US 9,757,042 B2
(45) Date of Patent: Sep. 12, 2017

(54) COMBINED FLOORMAT AND BODY-WORN PHYSIOLOGICAL SENSORS

(71) Applicant: TOSENSE, INC., La Jolla, CA (US)

(72) Inventors: Matthew Banet, San Diego, CA (US); Marshal Singh Dhillon, San Diego, CA (US); Susan Meeks Pede, Encinitas, CA (US); Lauren Nicole Miller Hayward, San Diego, CA (US); Arthur Deptala, Santee, CA (US); Jonas Dean Cochran, Santee, CA (US)

(73) Assignee: TOSENSE, INC., San Diego, CA (US)

( * ) Notice: Subject to any disclaimer, the term of this patent is extended or adjusted under 35 U.S.C. 154(b) by 0 days.

(21) Appl. No.: 14/988,683

(22) Filed: Jan. 5, 2016

(65) Prior Publication Data

US 2017/0188848 A1    Jul. 6, 2017

(51) Int. Cl.
| | | |
|---|---|---|
| *A61B 5/02* | (2006.01) |
| *A61B 5/053* | (2006.01) |
| *A61B 5/00* | (2006.01) |
| *A61B 5/1455* | (2006.01) |
| *A61B 5/01* | (2006.01) |
| *A61B 5/0205* | (2006.01) |
| *A61B 5/0452* | (2006.01) |
| *A61B 5/024* | (2006.01) |
| *A61B 5/021* | (2006.01) |

(52) U.S. Cl.
CPC ........ *A61B 5/02028* (2013.01); *A61B 5/0022* (2013.01); *A61B 5/01* (2013.01); *A61B 5/02055* (2013.01); *A61B 5/0452* (2013.01); *A61B 5/0535* (2013.01); *A61B 5/0537* (2013.01); *A61B 5/14552* (2013.01); *A61B 5/4872* (2013.01); *A61B 5/4875* (2013.01); *A61B 5/6802* (2013.01); *A61B 5/6892* (2013.01); *A61B 5/742* (2013.01); *A61B 5/02141* (2013.01); *A61B 5/02438* (2013.01); *A61B 2560/0223* (2013.01)

(58) Field of Classification Search
CPC ..... A61B 5/02028; A61B 5/0022; A61B 5/01; A61B 5/02055; A61B 5/0452; A61B 5/0535; A61B 5/0537; A61B 5/14552; A61B 5/4872; A61B 5/4875; A61B 5/6802; A61B 5/6892; A61B 5/742; A61B 5/02141; A61B 5/02438; A61B 2560/0223
See application file for complete search history.

(56) References Cited

U.S. PATENT DOCUMENTS 9,011,346 B2 *   4/2015   Wiard ................ A61B 5/02125
                                                      600/508

* cited by examiner

*Primary Examiner* — George Manuel
(74) *Attorney, Agent, or Firm* — Acuity Law Group, P.C.; Michael A. Whittaker

(57) ABSTRACT

The invention provides systems for measuring blood pressure and stroke volume values from a patient. Both systems feature a floormat system and a body-worn sensor working in concert. In aspects, the floormat generates calibrations for both blood pressure and stroke volume measurements. It features a base having a bottom surface configured to rest on or near a substantially horizontal surface, and a top surface configured to receive at least one of the patient's feet. Within the floormat are weight and blood pressure-measuring systems that determine, respectively, the calibrations for stroke volume and blood pressure. Its transmits these parameters to the body-worn sensor, which further processes them, along with other signals, to determine real-time values of blood pressure and stroke volume.

19 Claims, 15 Drawing Sheets

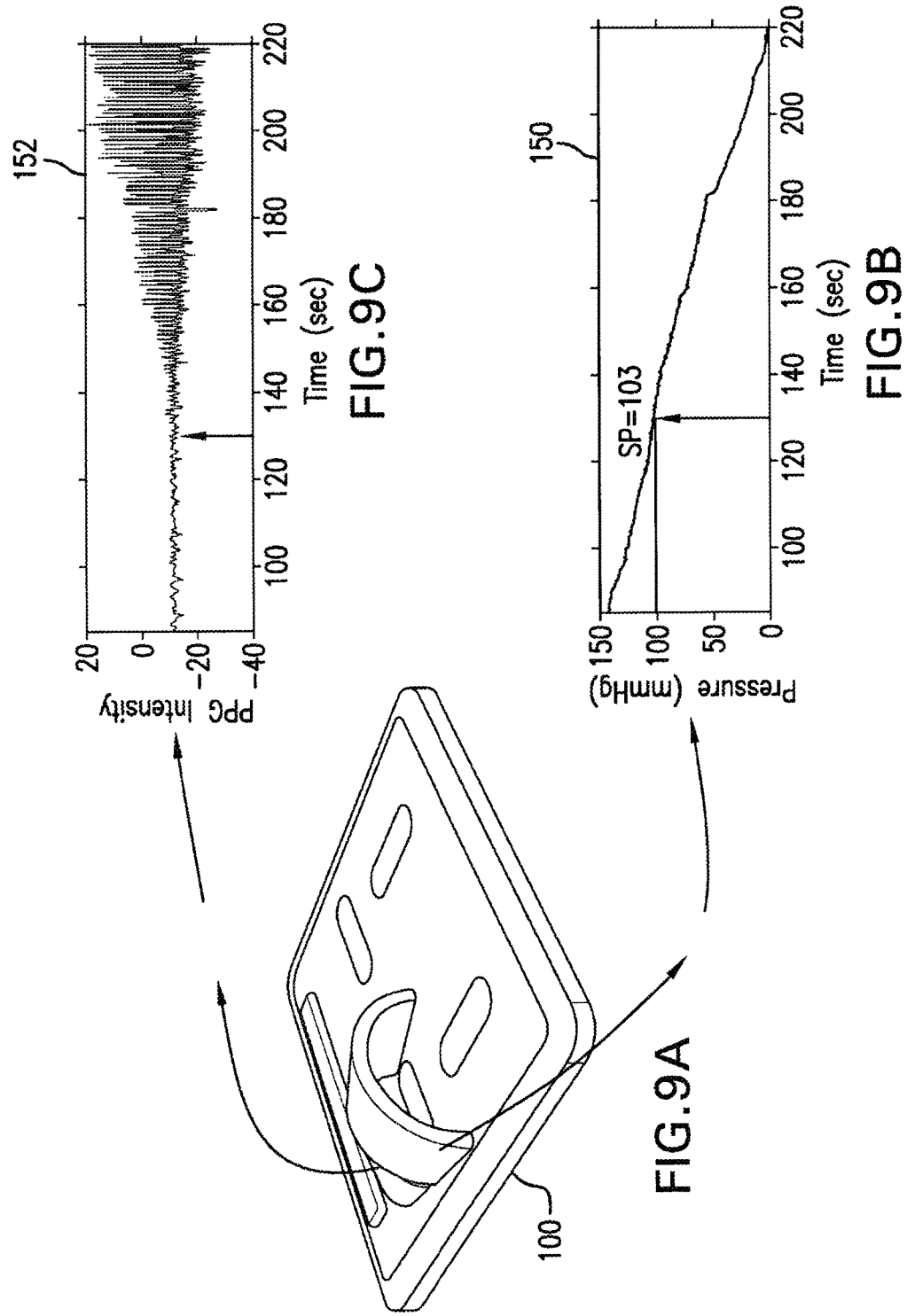

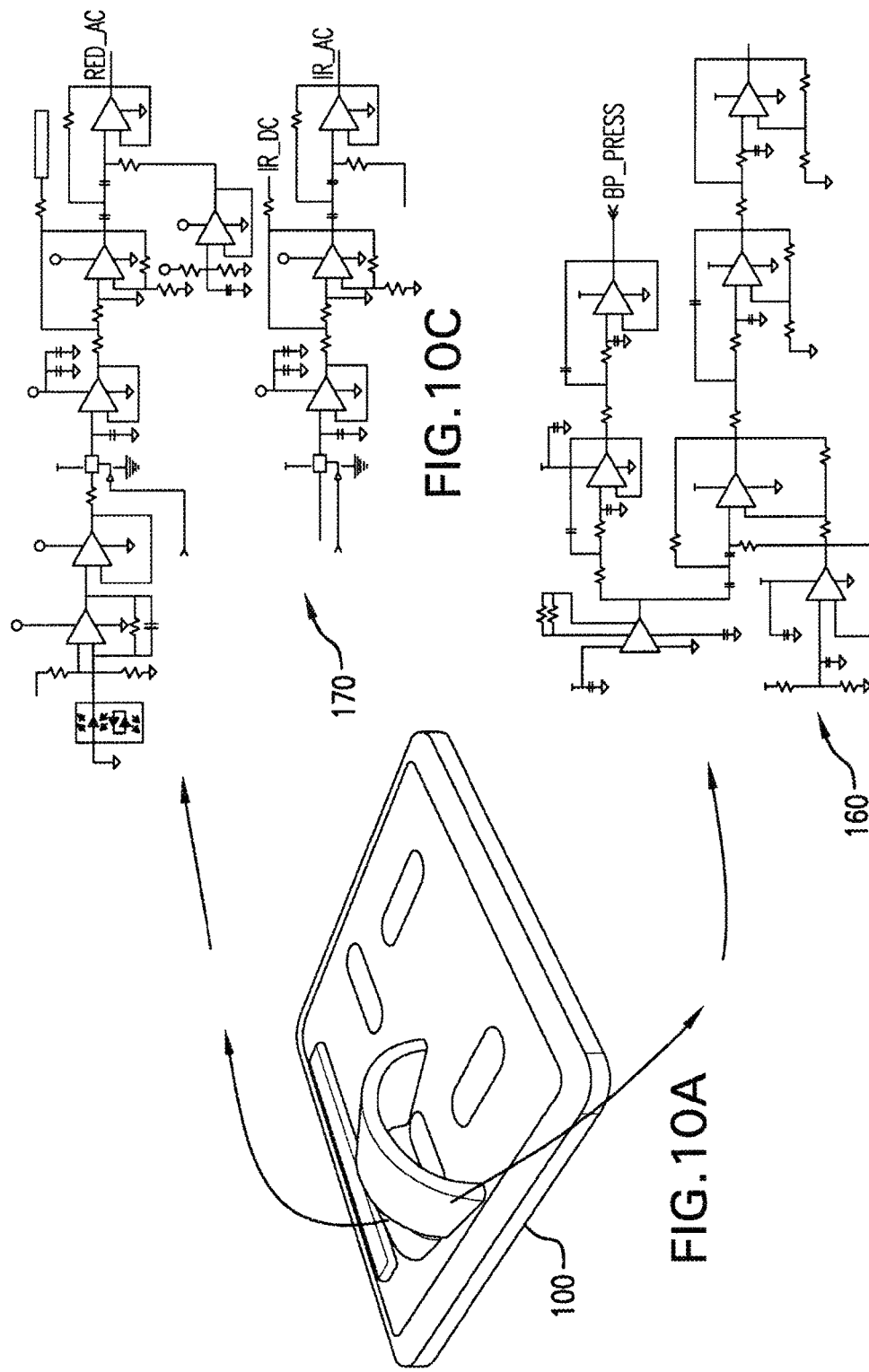

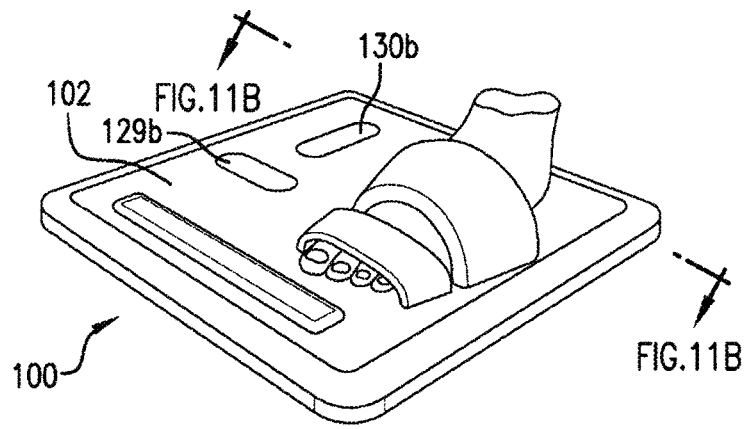
FIG.11A
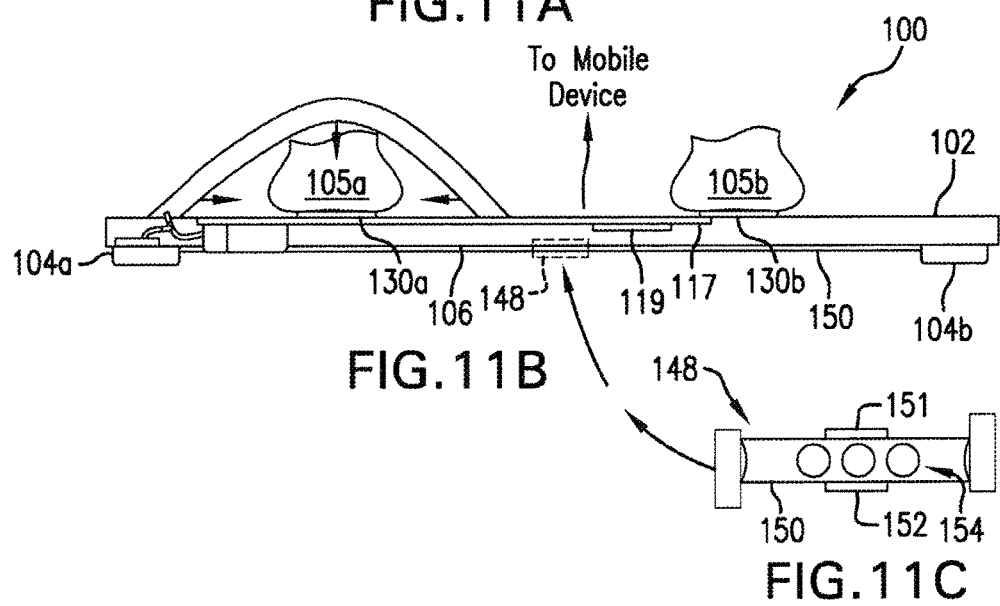
FIG.11B
FIG.11C
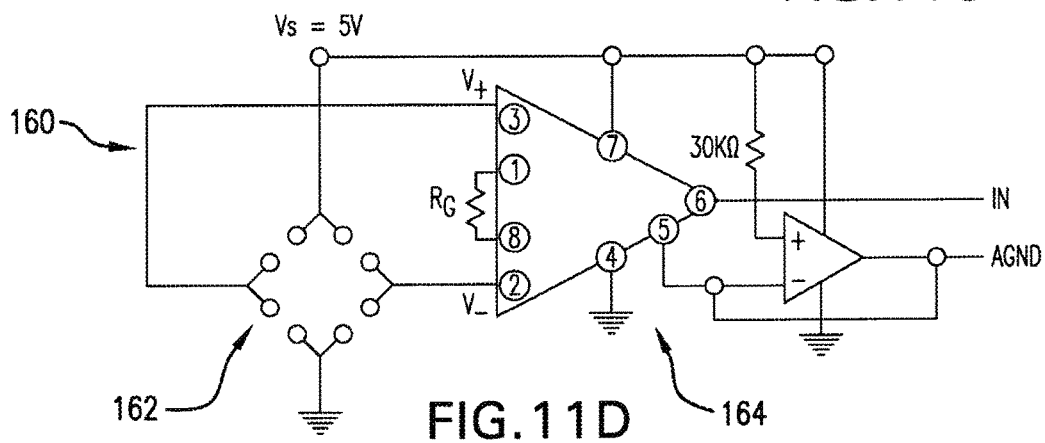
FIG.11D

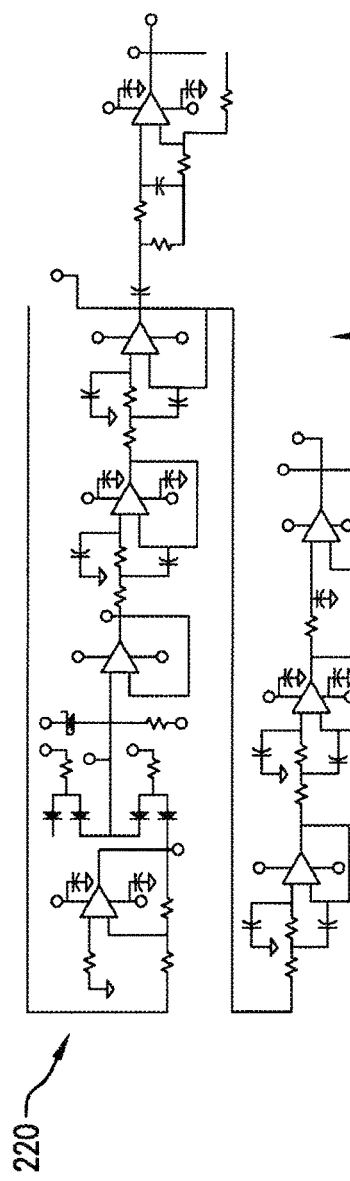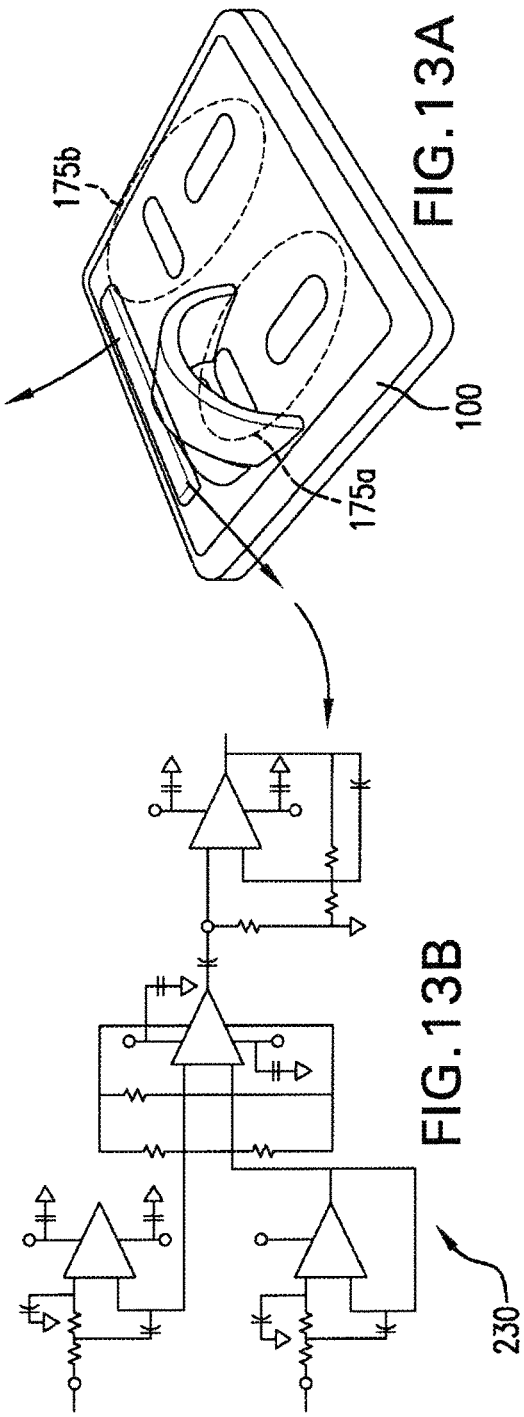

COMBINED FLOORMAT AND BODY-WORN PHYSIOLOGICAL SENSORS

BACKGROUND AND FIELD OF THE INVENTION

1. Field of the Invention

The invention relates to sensors that measure physiological signals from patients, and the use of such sensors.

2. General Background

Known electrical or digital weight scales typically use a load cell, integrated into a Wheatstone Bridge circuit, to measure a patient's weight. In such devices, the load cell exhibits a small, force-dependent resistance changes when the patient steps on the scale. The Wheatstone Bridge features four resistors, at least one of which is part of the load cell, and a measurable/ascertainable voltage change across Bridge varies with the force applied to the load cell. The voltage change thus correlates to the patient's weight. Once the scale is calibrated, the voltage is digitized and processed and ultimately converted into a weight, which is then displayed to the patient.

More advanced electrical or digital weight scales include stainless steel electrodes and associated circuitry to measure the patient's bioimpedance and/or bioreactance signals. Algorithms process parameters extracted from these signals to estimate parameters such as percent body fat and muscle mass.

Other known sensors measure physiological signals from a patient to determine time-varying waveforms, e.g. thoracic bioimpedance (TBI) and electrocardiogram (ECG) waveforms, with electrodes that attach to the patient's skin. These waveforms can be processed/analyzed to extract other medically relevant parameters such as heart rate (HR), respiration rate (RR), heart rate variability (HRV), stroke volume (SV), cardiac output (CO), and information relating to thoracic fluids, e.g. thoracic fluid index (TFC). Certain physiological conditions can be identified from these parameters using one-time measurements; other conditions require observation of time-dependent trends in the parameters in order to identify the underlying condition. In all cases, it is important to measure the parameters with high repeatability and accuracy.

Some conditions require various physiological parameters to be measured over a relatively short period of time in order to identify the condition. For example, Holter monitors can characterize various types of cardiac arrhythmias by measuring HR, HRV, and ECG waveforms over periods ranging from a day to a few weeks. On the other hand, chronic diseases such as congestive heart failure (CHF) and end-stage renal disease (ESRD) typically require periodic measurements of fluids and weight throughout the patient's life in order to identify the condition. Not surprisingly, patient compliance with measurement routines typically decreases as the measurement period increases. This is particularly true when measurements are made outside of a conventional medical facility, e.g., at the patient's home or in a residential facility such as a nursing home.

Furthermore, the measured values of some physiological parameters will vary with the location at which the parameters are measured, while those associated with other physiological parameters are relatively independent of the location at which the parameters are measured. For example, parameters such as HR, which depends on the time-dependent variation of R-R intervals in ECG waveforms, are relatively insensitive to sensor positioning. Likewise, pulse oximetry (SpO2) and pulse rate (PR), as measured with a pulse oximeter, show little variance with measurement location.

On the other hand, measurements that depend on amplitude-dependent features in waveforms, such as TFC, will be strongly dependent on the measurement location, e.g. the positioning of electrodes. In the case of TFC, for example, the measured value depends strongly on the sensed impedance between a set of electrodes. And this, in turn, will vary with the electrodes' placement. For TFC deviation in the day-to-day placement of the electrodes can result in measurement errors. This, in turn, can lead to misinformation (particularly when trends of the measured parameters are to be extracted), thereby nullifying the value of such measurements and thus negatively impacting treatment.

Like TFC, measured values of blood pressure (e.g. systolic (SYS) and diastolic (DIA) pressures), are typically sensitive to the location at which the parameter is measured. For example, blood pressure measured at the brachial artery with a sphygmomanometer (i.e. a manual blood pressure cuff) or with an oscillometric device (i.e. an automated blood pressure cuff) will typically be different from that measured at other locations on the body, such as the wrist, thigh, finger, or even the opposite arm. Body temperature (TEMP) is similarly dependent on the location at which it is measured.

3. Sensors, Devices, and Relevant Physiology

Disposable electrodes that measure ECG and TBI waveforms are typically worn on the patient's chest or legs and include: i) a conductive hydrogel that contacts the patient's skin; ii) a Ag/AgCl-coated eyelet that contacts the hydrogel; iii) a conductive metal post that connects to a lead wire or cable extending from the sensing device; and iv) an adhesive backing that adheres the electrode to the patient. Unfortunately, during a measurement, the lead wires can pull on the electrodes if the device is moved relative to the patient's body, or if the patient ambulates and snags the lead wires on surrounding objects. Such pulling can be uncomfortable or even painful, particularly where the electrodes are attached to hirsute parts of the body, and this can inhibit patient compliance with long-term monitoring. Moreover, these actions can degrade or even completely eliminate adhesion of the electrodes to the patient's skin, and in some cases completely destroying the electrodes' ability to sense the physiological signals at various electrode locations.

Some devices that measure ECG and TBI waveforms are worn entirely on the patient's body. These devices have been developed to feature simple, patch-type systems that include both analog and digital electronics connected directly to underlying electrodes. Such devices, like the Holter monitors described above, are typically prescribed for relatively short periods of time, e.g. for a period of time ranging from a day to several weeks. They are typically wireless and include features such as Bluetooth® transceivers to transmit information over a short distance to a second device, which then transmits the information via a cellular radio to a web-based system.

SpO2 values are almost always measured at the patient's fingers, earlobes, or, in some cases, toes. In these cases, patients wear an optical sensor to measure photoplethysmogram (PPG) waveforms, which are then processed to yield SpO2 and PR values. TEMP is typically measured with a thermometer inserted into the patient's mouth.

Assessing TFC, weight, and hydration status is important in the diagnosis and management of many diseases. For example, ESRD occurs when a patient's kidneys are no longer able to work at a level needed for day-to-day life. The disease is most commonly caused by diabetes and high blood pressure, and is characterized by swings in SYS and DIA along with a gradual increase in fluids throughout the body. Patients suffering from ESRD typically require hemodialysis or ultrafiltration to remove excess fluids. Thus, accurate measurement of TFC to identify ESRD can eliminate the need for empirical clinical estimations that often lead to over-removal or under-removal of fluid during dialysis, thereby preventing hemodynamic instability and hypotensive episodes (Anand et al., "*Monitoring Changes in Fluid Status With a Wireless Multisensor Monitor: Results From the Fluid Removal During Adherent Renal Monitoring (FARM) Study*," Congest Heart Fail. 2012; 18:32-36). A similar situation exists with respect to CHF, which is a complicated disease typically monitored using a "constellation" of physiological factors, e.g., fluid status (e.g. TFC), vital signs (i.e., HR, RR, TEMP, SYS, DIA, and SpO2), and hemodynamic parameters (e.g. CO, SV). Accurate measurement of these parameters can aid in managing patients, particularly in connection with dispensing diuretic medications, and thus reduce expensive hospital readmissions (Packer et al., "*Utility of Impedance Cardiography for the Identification of Short-Term Risk of Clinical Decompensation in Stable Patients With Chronic Heart Failure*," J Am Coll Cardiol 2006; 47:2245-52).

CHF is a particular type of heart failure (HF), which is a chronic disease driven by complex pathophysiology. In general terms, HF occurs when SV and CO are insufficient to adequately perfuse the kidneys and lungs. Causes of this disease are well known and typically include coronary heart disease, diabetes, hypertension, obesity, smoking, and valvular heart disease. In systolic HF, ejection fraction (EF) can be diminished (<50%), whereas in diastolic HF this parameter is typically normal (>65%). The common signifying characteristic of both forms of heart failure is time-dependent elevation of the pressure within the left atrium at the end of its contraction cycle, or left ventricular end-diastolic pressure (LVEDP). Chronic elevation of LVEDP causes transudation of fluid from the pulmonary veins into the lungs, resulting in shortness of breath (dyspnea), rapid breathing (tachypnea), and fatigue with exertion due to the mismatch of oxygen delivery and oxygen demand throughout the body. Thus, early compensatory mechanisms for HF that can be detected fairly easily include increased RR and HR.

As CO is compromised, the kidneys respond with decreased filtration capability, thus driving retention of sodium and water and leading to an increase in intravascular volume. As the LVEDP rises, pulmonary venous congestion worsens. Body weight increases incrementally, and fluids may shift into the lower extremities. Medications for HF are designed to interrupt the kidneys' hormonal responses to diminished perfusion, and they also work to help excrete excess sodium and water from the body. However, an extremely delicate balance between these two biological treatment modalities needs to be maintained, since an increase in blood pressure (which relates to afterload) or fluid retention (which relates to preload), or a significant change in heart rate due to a tachyarrhythmia, can lead to decompensated HF. Unfortunately, this condition is often unresponsive to oral medications. In that situation, admission to a hospital is often necessary for intravenous diuretic therapy.

In medical centers, HF is typically detected using Doppler/ultrasound, which measures parameters such as SV, CO, and EF. In the home environment, on the other hand, gradual weight gain measured with a simple weight scale is likely the most common method used to identify CHF. However, by itself, this parameter is typically not sensitive enough to detect the early onset of CHF—a particularly important stage in the condition when the condition may be ameliorated simply and effectively by a simple change in medication or diet.

SV is the mathematical difference between left ventricular end-diastolic volume (EDV) and end-systolic volume (ESV), and represents the volume of blood ejected by the left ventricle with each heartbeat; a typical value is about 70-100 mL. EF relates to EDV and ESV as described below in Eq. 1:

$$EF = \frac{SV}{EDV} = \frac{EDV - ESV}{EDV} \qquad (1)$$

CO is the average, time-dependent volume of blood ejected from the left ventricle into the aorta and, informally, indicates how efficiently a patient's heart pumps blood through their arterial tree; a typical value is about 5-7 L/min. CO is the product of HR and SV, i.e., $$CO = SV \times HR \qquad (2)$$

CHF patients—particular those suffering from systolic HF—may receive implanted devices such as pacemakers and/or cardioverter-defibrillators to increase EF and subsequent blood flow throughout the body. These devices may include circuitry and algorithms to measure the electrical impedance between different leads of the device. Some implanted devices process this impedance to calculate a "fluid index". As thoracic fluid increases in the CHF patient, the impedance typically is reduced, and the fluid index increases. Thus, the fluid index, when read by an interrogating device placed outside the patient's body, can indicate the onset of heart failure.

4. Clinical Solutions

Many of the above-mentioned parameters can be used as early markers or indicators that signal the onset of CHF. EF is typically low in patients suffering from this chronic disease, and it can be further diminished by factors such as a change in physiology, an increase in sodium in the patient's diet, or non-compliance with medications. This is manifested by a gradual decrease in SV, CO, and SYS that typically occurs between two and three weeks before hospitalization becomes necessary to treat the condition. The reduction in SV and CO diminishes perfusion to the kidneys. As noted above, these organs then respond with a reduction in their filtering capacity, thus causing the patient to retain sodium and water and leading to an increase in intravascular volume. This, in turn, leads to congestion, which is manifested to some extent by a build-up of fluids in the patient's thoracic cavity (e.g. TFC). Typically, a detectable increase in TFC occurs about 1-2 weeks before hospitalization becomes necessary. Body weight increases after this event (typically by between three and five pounds), thus causing fluids to shift into the lower extremities. At this point, the patient may experience an increase in both HR and RR to increase perfusion. Nausea, dyspnea, and weight gain typically grow more pronounced a few days before hospitalization becomes necessary. As noted above, a characteristic of decompensated HF is that it is often unresponsive to oral medications; thus, at this point, intravenous diuretic therapy in a hospital setting often becomes mandatory. A hospital stay for intravenous diuretic therapy typically lasts about 4 days, after which the patient is discharged and the above-described cycle may start over once again.

Such cyclical pathology and treatment is physically taxing on the patient, and economically taxing on society. In this regard, CHF and ESRD affect, respectively, about 5.3 million and 3 million Americans, resulting in annual healthcare costs estimated at $45 billion for CHF and $35 billion for ESRD. CHF patients account for approximately 43% of annual Medicare expenditures, which is more than the combined expenditures for all types of cancer. Somewhat disconcertingly, roughly $17 billion of this is attributed to hospital readmissions. CHF is also the leading cause of mortality for patients with ESRD, and this demographic costs Medicare nearly $90,000/patient annually. Thus, there understandably exists a profound financial incentive to keep patients suffering from these diseases out of the hospital. Starting in 2012, U.S. hospitals have been penalized for above-normal readmission rates. Currently, the penalty has a cap of 1% of payments, growing to over 3% in the next three years.

Of some promise, however, is the fact that CHF-related hospital readmissions can be reduced when clinicians have access to detailed information that allows them to remotely titrate medications, monitor diet, and promote exercise. In fact, Medicare has estimated that 75% of all patients with ESRD and/or CHF could potentially avoid hospital readmissions if treated by simple, effective programs.

Thus, in order to identify precursors to conditions such as CHF and ESRD, physicians can prescribe physiological monitoring regimens to patients living at home. Typically, such regimens require the use of multiple standard medical devices, e.g. blood pressure cuffs, weight scales, and pulse oximeters. In certain cases, patients use these devices daily and in a sequential manner, i.e., one device at a time. The patient then calls a central call center to relay their measured parameters to the call center. In more advanced systems, the devices are still used in a sequential manner, but they automatically connect through a short-range wireless link (e.g. a Bluetooth® system) to a "hub," which then forwards the information to a call center. Often, the hub features a simple user interface that presents basic questions to the patient, e.g. questions concerning their diet, how they are feeling, and whether or not medications were taken.

Ultimately, however, and regardless of how sophisticated such instrumentation may be, in order for such monitoring to be therapeutically effective, it is important for the patient to use their equipment consistently, both in terms of the duration and manner in which it is used. Less-than-satisfactory consistency with the use of any medical device (in terms of duration and/or methodology) may be particularly likely in an environment such as the patient's home or a nursing home, where direct supervision may be less than optimal.

SUMMARY OF THE INVENTION

In view of the foregoing, it would be beneficial to provide a monitoring system that is suitable for home use. Particularly valuable would be a system featuring multiple devices that communicate with each other wirelessly in order to conveniently measure a collection of vital signs and hemodynamic parameters. Ideally, such a system is easy to use and features a simple form factor that integrates into the patient's day-to-day activities. The monitoring system according to the invention, which facilitates monitoring a patient for HF, CHF, ESRD, cardiac arrhythmias, and other diseases, is designed to achieve this goal.

More specifically, the monitoring system is comprised of two primary components or devices: one component/device is configured like a floormat or conventional weight-measuring scale, and therefore is referred to herein as 'the floormat'. The second component/device is worn on the body, and is referred to herein as 'the body-worn sensor'. Collectively the floormat and body-worn sensor measure and/or calculate a collection of vital signs along with the sophisticated hemodynamic parameters discussed above. Measurements typically take on the order of two or three minutes to complete, after which information is then wirelessly transmitted through a gateway (e.g. a mobile device, such as a smartphone or tablet computer) to a web-based system, where it can be viewed, e.g., by patients, clinicians, and family members. Gateways that are mobile phones or tablet computers can also display numerical values, waveforms, graphs, etc.

In a more general sense, the floormat measures patient-specific calibrations, and then wirelessly transmits them to the body-worn sensor, which processes them to determine values of BP and SV.

Preferably the monitoring system is used daily, and collects information that can be analyzed to determine time-dependent trends. The information it collects may be analyzed to detect the early onset of many diseases, e.g. CHF. Ultimately, the floormat can provide clinicians with information that, when acted on, may prevent hospitalization.

In general, the parameters measured by the floormat and then used by algorithms in the body-worn sensor to calculate SV and BP are not available from conventional weight scales. For SV, such parameters (referred to herein as a 'SV calibration') include weight and a detailed body composition measured through a combination of bioimpedance and bioreactance. For BP, such parameters (referred to here as a 'BP calibration') include initial values of SYS, DIA, MAP, and a patient-specific relationship between changes in BP (or BP alone) and transit times such as pulse arrival time (PAT), pulse transit time (PTT), and/or vascular transit time (VTT). Both the SV and BP calibrations are described in more detail, below.

More particularly, the combined floormat and body-worn sensor measure the following parameters from a patient: HR, PR, SpO2, RR, SYS, DIA, TEMP, a thoracic fluid index (TFI), SV, CO, weight, percent body fat, muscle mass, and parameters sensitive to blood pressure such as PAT, PTT, and VTT.

Both the floormat and body-worn sensor include digital processing system featuring a microprocessor, a wireless transmitter, and an analog-to-digital converter processes signals measured/generated by the corresponding sensor of each of the various subsystems to determine the associated physiological information described above. Rechargeable batteries power both systems.

In one aspect, the invention provides a system for measuring a blood pressure value from a patient. The invention features a floormat system and a body-worn sensor that work in concert to perform the measurement. More specifically, the floormat generates a blood pressure calibration. It features a base having a bottom surface configured to rest on or near a substantially horizontal surface, and a top surface configured to receive at least one of the patient's feet. A pressure-delivery system within the floormat connects to the top surface and features an opening which covers a portion of at least one of the patient's feet when it is in contact with the top surface. The pressure-delivery system typically includes a flexible member that applies pressure to a portion of at least one of the patient's feet, and a pressure sensor that measures the applied pressure. A processing system in electrical contact with the pressure sensor receives signals from the pressure sensor and converts them into a set of pressure values, and then analyzes the set of pressure values to determine the blood pressure calibration, which is described in more detail below.

The body-worn sensor includes independent systems for measuring first and second time-dependent waveforms from the patient, and a processing system that analyzes the waveforms to determine first and second fiducial points. It also includes a computer-controlled system that receives the blood pressure calibration from the floormat. Once this information is received, the processing system analyzes the first and second fiducial points to determine a transit time, and then further processes the transit time and the blood pressure calibration to determine a blood pressure value.

In embodiments, the blood pressure calibration includes values of SYS, DIA, and MAP. In other embodiments, the calibration includes a patient-specific relationship between a transit time and blood pressure.

Typically the floormat and body-worn sensor include paired wireless transmitters for, respectively, sending and receiving the blood pressure calibration. In preferred embodiments the transmitters are based on Bluetooth® or 802.11.

In embodiments, the flexible member is a bladder (that can be filled, e.g., with a fluid such as air), and the pressure-delivery system includes a pump. The pump connects to the bladder and, in embodiments, a valve, and is configured to pump air into the bladder when the pump is powered on. The pressure sensor connects to the bladder and is configured to measure a pressure within the bladder. In embodiments, the bladder is formed as a strap that receives air from the pump, with a first distal end of the strap connected to the top surface, and a second distal end of the strap connected to the top surface.

Typically the processing system features computer code that analyzes the set of pressure values to determine the blood pressure value. The computer code can run on, e.g., a microcontroller or microprocessor. For example, the pressure values can be a set of pressure-dependent oscillations that depend on the patient's blood pressure, and the computer code can analyze these to determine a blood pressure value. Typically, each pressure-dependent oscillation in the set of pressure-dependent oscillations is characterized by a pressure and amplitude value, and the computer code is further configured to determine the pressure-dependent oscillation having a maximum amplitude value. From this the system calculates the MAP. In related embodiments, the computer code is further configured to determine SYS from a first pressure-dependent oscillation characterized by an amplitude that, when divided by the maximum amplitude of the pressure-dependent oscillations, is substantially equivalent to a first pre-determined ratio (typically between 0.4-0.8, and most preferably about 0.6). In yet another related embodiment, the computer code is further configured to determine DIA from a second pressure-dependent oscillation characterized by an amplitude that, when divided by the maximum amplitude of the pressure-dependent oscillations, is substantially equivalent to a second pre-determined ratio (typically between 0.4-0.8, and most preferably about 0.7).

In embodiments, the set of pressure-dependent oscillations are measured while the pressure-delivery system inflates or deflates the flexible member.

In another aspect, the invention features a system for measuring a stroke volume value from a patient that, similar to the above-described invention, features a floormat and body-worn sensor that work in concert to make the measurement. Here, the floormat measures a stroke volume calibration, and then transmits this to the body-worn sensor for follow-on processing. The floormat features a weight-measuring system featuring at least one strain gauge, and a processing system that receives an output signal (or a signal derived from the output signal) from the strain gauge. The processing system analyzes this signal to determine the stroke volume calibration, which it then transmits to the body-worn sensor with a first wireless system.

The body-worn sensor features an electrical impedance system having at least four electrodes, at least one of which is configured to inject an electrical current into the patient's body, and at least one of which is configured to measure a signal induced by the electrical current and representative of an impedance plethysmogram. A second wireless system within the sensor receives the stroke volume calibration. And an internal processing system receives signals from the electrical impedance system and converts them into a set of impedance values, and then analyzes the set of impedance values and the stroke volume calibration to calculate the stroke volume value.

In embodiments, the stroke volume calibration includes a value representing the patient's weight and/or body composition. These values are used to calculate a volume conductor, described in more detail below.

In other embodiments, the electrical system within the weight-measuring system features a Wheatstone Bridge that connects electrically with an amplifier system. Here, the system's processing system is further configured to receive the set of voltages, and analyze them to determine a value of weight corresponding to the force applied on the top surface.

In other embodiment, the electrical impedance system features an electrical system that injects a current modulated at a frequency between 25-125 kHz (and preferably about 100 kHz). Typically the electrical impedance system features two electrodes that inject the electrical current that are disposed on the structure's top surface, with one electrode located substantially on the left-hand side of the top surface and configured to inject electrical current into the left-hand side of the patient's chest, and one electrode located substantially on the right-hand side of the top surface and configured to inject electrical current into the right-hand side of the patient's chest. It also typically includes two additional electrodes, each configured to measure a signal induced by the electrical current, wherein the electrodes are located on the left and right-hand side of the patient's chest.

In embodiments, the processing system features computer code configured to analyze the set of impedance values to determine the stroke volume value. For example, the computer code can calculate a derivative of the set of impedance values to determine a $d\Delta Z(t)/dt$ waveform, from which it calculates a maximum value or an area of a pulse therein. The computer code can also analyze the $d\Delta Z(t)/dt$ waveform to determine an ejection time or a baseline impedance ($Z_o$) value. The computer code can then process these values to determine SV using Eq. 3:

$$SV \sim \frac{(d\Delta Z(t)/dt)_{max}}{Z_o} \times LVET \tag{3}$$

or, alternatively:

$$SV \sim \sqrt{\frac{(d\Delta Z(t)/dt)_{max}}{Z_o}} \times LVET \tag{4}$$

In embodiments, the system's weight-measuring system measures a set of voltages that correlates with a force applied to the top surface, and from these calculate the user's weight. The processing system can then use the weight to determine SV from the equation:

$$SV = V_c \times \frac{(d\Delta Z(t)/dt)_{max}}{Z_o} \times LVET \qquad (5)$$

or, alternatively:

$$SV = V_c \times \sqrt{\frac{(d\Delta Z(t)/dt)_{max}}{Z_o}} \times LVET \qquad (6)$$

where $V_c$ is a volume conductor calculated from the value of weight and/or body composition.

In still other aspects, the system calculates CO by also measuring HR as described below (e.g. using an ECG waveform), and then collectively processing SV and HR (e.g., by taking the product) to determine CO.

In another aspect, the body-worn sensor measures a PTT value from a patient, and then uses this and the blood pressure calibration to determine the patient's blood pressure value. In this aspect the body-worn sensor features: 1) a mechanical structure similar to that described above; 2) an electrical impedance system similar to that described above that generates a first set of signals representative of an impedance plethysmogram; 3) a heart rate monitoring system connected to the mechanical structure and featuring a differential amplifier configured to measure a second set of signals representative of a cardiac rhythm from the patient; and 4) a processing system in electrical contact with the electrical impedance system and the heart rate monitoring system, and configured to: i) receive the first signals from the electrical impedance system and convert them into a set of impedance values; ii) analyze the set of impedance values to determine a first time value indicating a first pulsatile component; iii) receive the second set of signals from the heart rate monitoring system and convert them into a set of cardiac rhythm values; iv) analyze the set of cardiac rhythm values to determine a second pulsatile component; and v) collectively process the first and second pulsatile components to determine the PTT value.

In embodiments, the processing system features computer code configured to: i) calculate a mathematical derivative of the impedance values to determine a set of derivative values; and ii) determine a local maximum of the set of derivative values to determine the first pulsatile component; and/or iii) determine a zero-point crossing of the set of derivative values to determine the first pulsatile component. The computer code may also be configured to: i) estimate the set of derivative values with a mathematical function; and ii) analyze the mathematical function to determine the first pulsatile component.

In embodiments, the computer code is configured to determine a local maximum of the cardiac rhythm values to determine the second pulsatile component, and the cardiac rhythm values are representative of an ECG waveform. For example, the computer code can be configured to determine a QRS complex (e.g. calculate the Q or R point) in the ECG waveform to determine the second pulsatile component. It can also further process the cardiac rhythm values to determine a heart rate value, e.g. by calculating a time interval separating the first and second R points.

In a related aspect, the invention provides a system for measuring a PTT value from a patient that is similar to that described above, but also includes an optical system for measuring a photoplethysmogram from the patient's body. This system may be used in place or in addition to the impedance system. The processing system analyzes photoplethysmogram to determine a pulsatile component, which it then processes to determine the PTT value. In general, the system may use any combination of pulsatile components measured from cardiac rhythm waveforms (e.g., ECG waveforms), impedance plethysmogram waveforms, and photoplethysmogram waveforms to determine a PTT value.

The measurement system described herein has many advantages. Collectively, the floormat and body-worn sensor provide a single, easy-to-use device that a patient can use to measure all their vital signs, complex hemodynamic parameters, and basic wellness-related parameters such as weight, percent body fat, and muscle mass. Such ease of use may increase compliance, thereby motivating patients to use it every day. And with daily use, the measurement system can calculate trends in a patient's physiological parameters, thereby allowing better detection of certain disease states and/or management of chronic conditions such as CHF, diabetes, hypertension, COPD, kidney failure, and/or obesity.

Because of its form-factor/configuration and associated modality of use (i.e., simply stepping onto and standing on it), the floormat helps ensure consistent measurement of the various parameters through the patient's feet when used on a daily basis, thereby improving the repeatability and reproducibility of its measurements. This is particularly true given the general similarity of the floormat to a conventional bathroom scale—something most people are used to using on a weekly or even daily basis to determine their health (i.e., weight) status.

The body-worn sensor, when combined with the floormat, can make both one-time measurements (e.g. resting HR, SV, CO, and/or SYS, DIA, and MAP) and continuous measurements (e.g., continuously measured HR and activity levels) to track a patient's fitness level or progression of a specific disease state. Likewise, data from the measurement system can be combined with video or still images from cameras within the patient's home to monitor a patient by collectively processing physiological information along with that indicating their at-home activities (e.g., how much they are eating, sleeping, watching television, etc.). Such information, for example, may indicate the onset of a physiological condition that may require a medical event, e.g. hospitalization.

Still other advantages should be apparent from the following detailed description and from the claims.

BRIEF DESCRIPTION OF THE DRAWINGS

FIG. 9A is a rear perspective view of the floormat shown in FIG. 6A;

FIG. 9B is a plot illustrating a pressure waveform generated by a blood pressure system housed within the floormat of FIG. 6A;

FIG. 9C is a plot illustrating a PPG waveform generated by an optical system housed within the floormat of FIG. 6A;

FIG. 10A is a rear perspective view of the floormat shown in FIG. 6A;

FIG. 10B is a schematic circuit diagram illustrating the blood pressure system of the floormat of FIG. 6A;

FIG. 10C is a schematic circuit diagram illustrating the optical system of the floormat of FIG. 6A;

FIG. 11A is a front perspective view of the floormat shown in FIG. 6B;

FIG. 11B is a schematic section view along the sight-line 11B in FIG. 11A;

FIG. 11C is a schematic representation of the weight-measuring load cell shown in FIG. 11B;

FIG. 11D is a schematic circuit diagram illustrating the Wheatstone Bridge used in connection with the load cell of FIG. 11C to measure patient weight;

FIG. 13A is a rear perspective view of the floormat shown in FIG. 6A;

FIG. 13B is a schematic diagram of a circuit for generating and processing ECG waveforms;

FIG. 13C is a schematic diagram of a circuit for generating and processing BI waveforms;

DETAILED DESCRIPTION

1. Product Overview

The invention provides a floormat and body-worn sensor that operate in concert to measure information related to a patient's vital signs, hemodynamic parameters, and body composition. More specifically, the floormat measures parameters used in algorithms on the body-worn sensor for calculating SV and BP. The two systems communicate wirelessly (using, e.g., pair Bluetooth® transceivers) so that the floormat can transmit parameters to the body-worn system, which then processes them as described above.

In general, the parameters measured by the floormat and then used by algorithms in the body-worn sensor to calculate SV and BP are not available from conventional weight scales. For SV, such parameters (referred to herein as a 'SV calibration') include weight and a detailed body composition measured through a combination of bioimpedance and bioreactance. For BP, such parameters (referred to here as a 'BP calibration') include initial values of SYS, DIA, MAP, and a patient-specific relationship between changes in BP (or BP alone) and transit times such as PAT, PTT and/or VTT. Both the SV and BP calibrations are measured from the user's feet, and are described in more detail, below.

Figure 1:
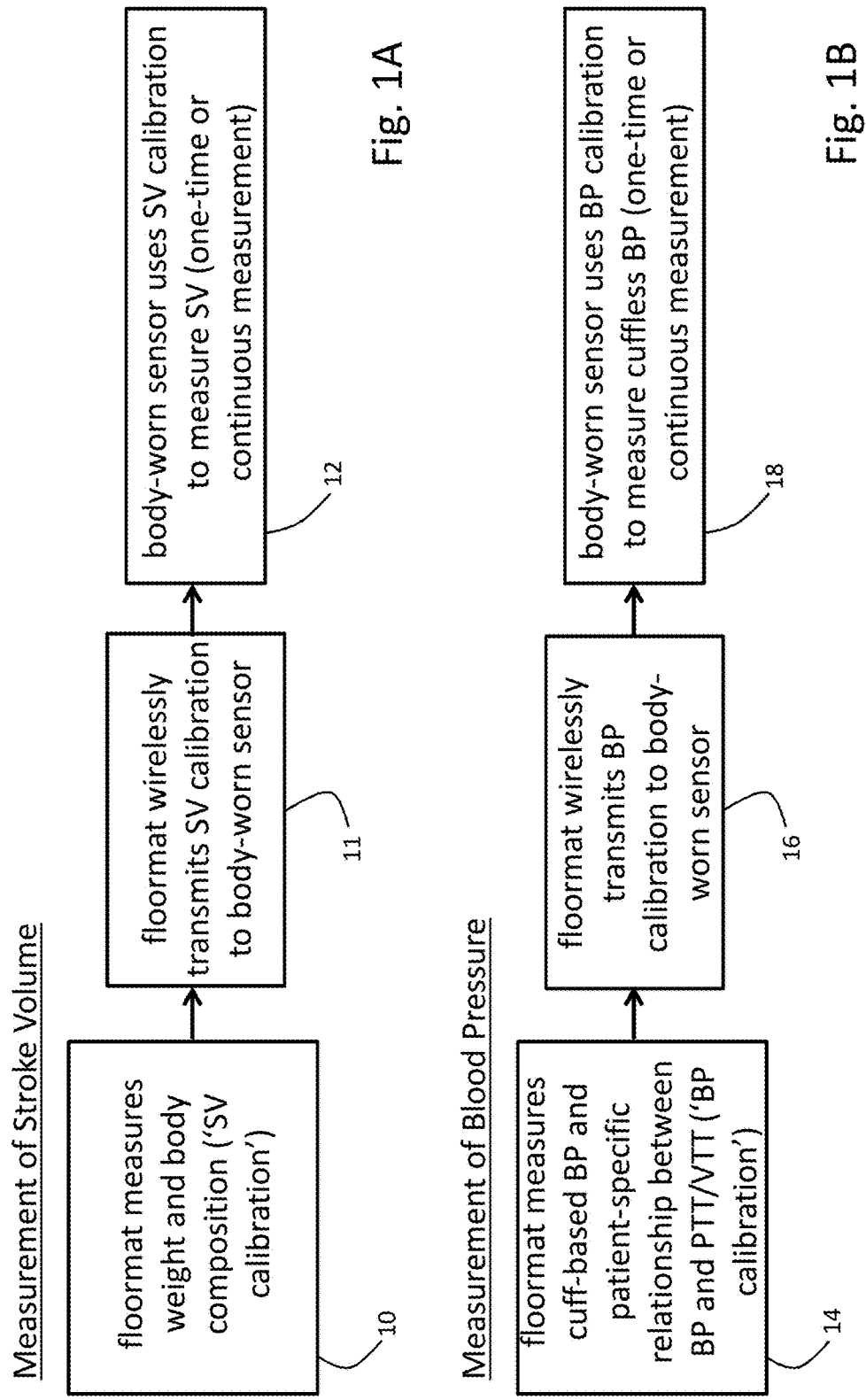
FIG. 1A is a flow chart outlining the communication process between the floormat and body-worn sensor so that these devices can measure SV.
FIG. 1B is a flow chart outlining the communication process between the floormat and body-worn sensor so that these devices can measure blood pressure.

FIGS. 1A and 1B include a flow chart showing typical use of the floormat and body-worn sensor. During a typical use, a user wears the body-worn sensor, which is preferably shaped like a necklace as is described in more detail below, by draping it around their shoulders and adhering its electrodes to their chest. The user then steps on the floormat like they would a conventional weight scale. This activates a computer-controlled system within the floormat, thus controlling it to measure SV and BP calibrations (steps 10, 14). This process takes about 30 seconds. The computer-controlled system also controls an internal Bluetooth® transceiver which communicates with a paired Bluetooth® transceiver in the body-worn sensor. Once the Bluetooth® transceivers are paired, BP and SV calibrations measured by the floormat wirelessly transmit to the body-worn sensor (steps 11, 16). The body-worn sensor receives the SV and BP calibrations, and then processes them along with signals that it measures independently on the floormat to calculate SV and BP, as described below. Using this process, the body-worn sensor can make a single measurement of SV and BP. Alternatively, it can measure these parameters in a quasi-continuous manner, e.g. periodically or episodically.

Figure 2:
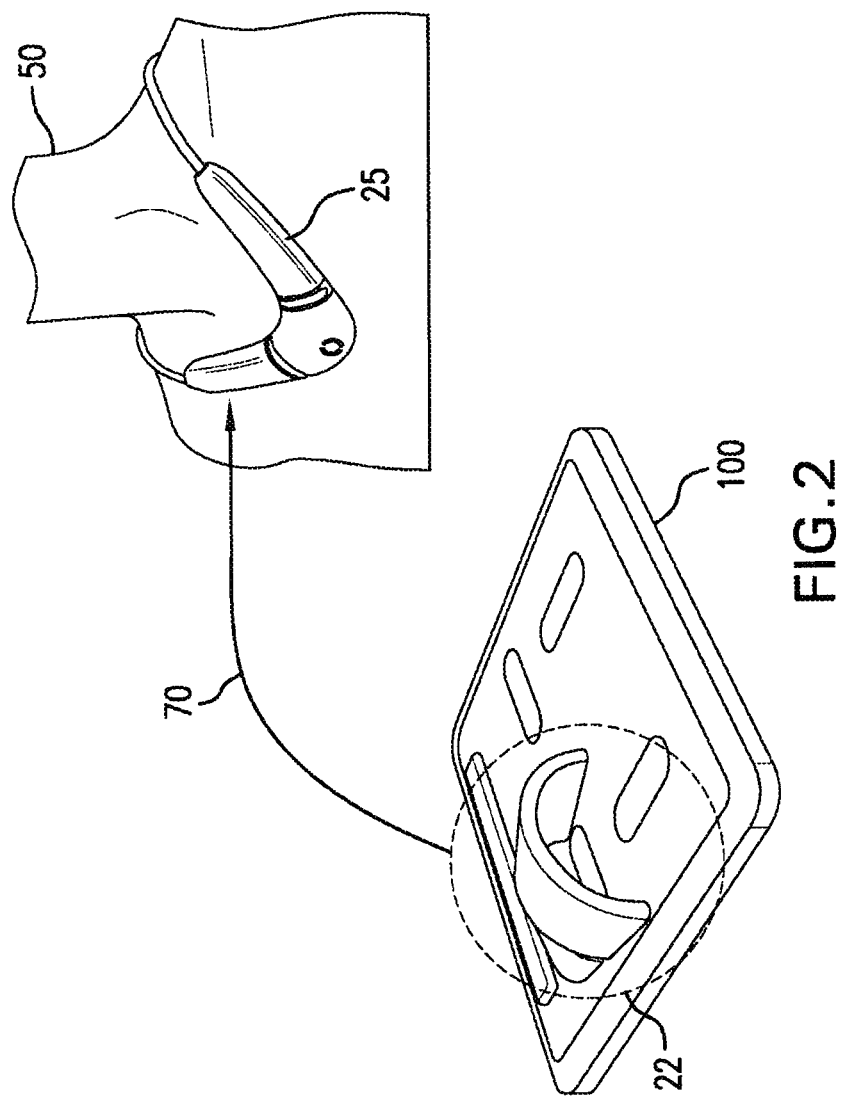
FIG. 2 is a three-dimensional view of the floormat and its cuff-based system communicating directly with the necklace-shaped sensor.

FIG. 2 shows images of a preferred floormat 100 and body-worn sensor 25 as used in the invention.

More specifically, FIGS. 2-5 show a body-worn sensor 25 that can be used according to the invention to monitor a patient suffering from HF, CHF, ESRD, cardiac arrhythmias, and other diseases in both home and clinical environments. The body-worn sensor 25 is worn like a conventional necklace, comfortably around the neck, and features a mechanical mechanism that ensures consistent placement when used on a daily basis, thereby improving the repeatability and reproducibility of its measurements. Additionally, the sensor 25 makes simultaneous measurements of multiple parameters, and thus obviates the need to use multiple devices. Both of these features may improve patient compliance.

The sensor 25 is able to detect the early onset of these and other diseases, thereby providing clinicians information that, when acted on, may prevent hospitalization. More particularly, the invention features a neck-worn sensor that is an integrated, body-worn system, which measures the following parameters from a patient: HR, PR, SpO2, RR, BP, TEMP, TFI, SV, and CO, as is described in detail below. Thus, the sensor, when used in combination with the floormat, can measure all five vital signs (HR/PR, SpO2, RR, TEMP, and SYS/DIA) along with hemodynamic parameters (SV, CO, TFI). Trends in some of these parameters, e.g. SV, SYS, and TFI, may predict the onset of HF (e.g. CHF) before its severity is such that the patient requires admission to a hospital. By measuring this constellation of properties in the patient's home and then wirelessly transmitting them to a clinician for evaluation, the sensor facilitates timely medical intervention that may ultimately keep the patient out of the hospital.

The sensor also includes a motion-detecting accelerometer, from which it can determine motion-related parameters such as posture, degree of motion, activity level, respiratory-induced heaving of the chest, and falls. The sensor can operate additional algorithms to process the motion-related parameters to measure vital signs and hemodynamic parameters when motion is minimized and below a pre-determined threshold, thereby reducing artifacts. Moreover, the sensor estimates motion-related parameters such as posture to improve the accuracy of calculations for vital signs and hemodynamic parameters.

Disposable electrodes attach directly to the sensor to secure it in close proximity to the patient's body without bothersome cables. In particular, the electrodes are provided in patches, with each electrode patch containing two electrode regions to measure ECG and TBI waveforms. The patches easily and releasably connect to circuit boards contained within the sensor by means of magnets that are electrically connected to the circuit boards to provide signal-conducting electrical couplings. Prior to use, the electrodes are simply held near the circuit boards, and magnetic attraction causes the electrode patches to snap into proper position, thereby ensuring proper positioning of the electrodes on the patient's body.

Using light-emitting diodes operating in the red (e.g. 600 nm) and infrared (e.g. 800 nm) spectral regions, the sensor measures SpO2 and PR by pressing lightly against capillary beds in the patient's chest. Operating in a reflection-mode geometry, the sensor measures PPG waveforms with both red and infrared wavelengths. SpO2 is processed from alternating and static components of these waveforms. PR, in turn, can be calculated from neighboring pulses, typically from the PPG waveform generated with infrared light, as this typically has a relatively high signal-to-noise ratio.

All analog and digital electronics associated with these various measurements are directly integrated into the body-worn sensor. This means that a single, unobtrusive component—shaped like a piece of conventional jewelry instead of a bulky medical device—measures a robust set of parameters that can characterize a patient using both one-time and continuous measurements. Measurements can take place over just a few minutes or several hours, and can be made in medical facilities and at home. The body-worn sensor includes a simple LED in its base (i.e. sensing) portion, which is located near the center of the chest when worn by the patient. The sensor also includes a wireless transmitter (operating Bluetooth® and/or 802.11a/b/g/n) than sends data to, e.g., a conventional mobile device (e.g. cellular telephone, tablet computer, desktop/laptop computer, or plug-in hub).

The sensor is lightweight (about 100 grams) and battery-powered. During use, it simply drapes around the neck, where the disposable electrodes hold it in place. Flexible, conductive elements resembling strands in a conventional necklace power on the sensor, hold it in place, and also ensure that it is consistently positioned when used on a daily basis. Moreover, the patient's neck is a location that is unobtrusive, comfortable, removed from the hands, and able to bear the weight of the sensor without being noticeable to the patient. The neck and thoracic cavity are also relatively free of motion compared to appendages such as the hands and fingers, and thus a sensor affixed to the neck region minimizes motion-related artifacts. Moreover, such artifacts are compensated for, to some degree, by the accelerometer within the sensor. And because the sensor resembles jewelry (e.g., a necklace) and is therefore considerably less noticeable or obtrusive than various prior-art devices, emotional discomfort over wearing a medical device over an extended period of time is reduced, thereby fostering long-term patient compliance with a monitoring regimen.

The sensor's form factor is designed for comfort and ease of use, with the ultimate goal of improving patient compliance so that the above-mentioned parameters can be measured in a continuous manner and on a day-to-day basis. The system is targeted for elderly, at-home patients, e.g. those suffering from chronic conditions such as HF, CHF, ESRD and related cardiac diseases, diseases of the kidneys, diabetes, and chronic obstructive pulmonary disease (COPD).

The floormat 100 in FIG. 2 includes a cuff-based system 22 disposed on its top surface to measure the BP calibration. Once measured, and as indicated by arrow 70, the Bluetooth® transceiver within them floormat wireless transmits the BP calibration directly to a paired Bluetooth® transceiver within the body-worn sensor 25, which is worn by a user 25. The body-worn sensor then processes the BP calibration as described in more detail below to make one-time or quasi-continuous measurements of BP without using a similar cuff-based system.

Figure 4:
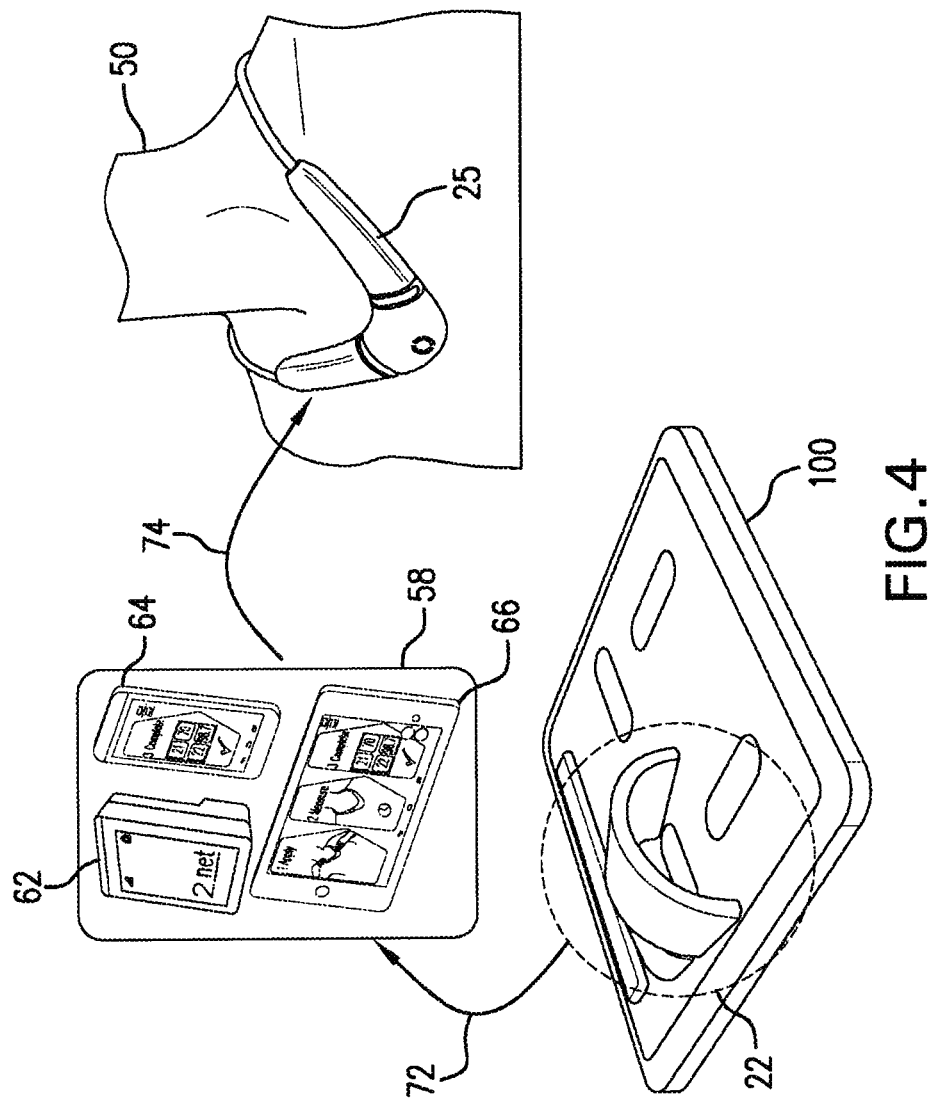
FIG. 4 is a three-dimensional view of the floormat and its cuff-based system communicating through a wireless gateway with the necklace-shaped sensor.

Alternatively, as shown in FIG. 4 and indicated by arrows 72, 74, the Bluetooth® transceiver within the floormat can send the BP calibration to an external wireless device 58, such as a tablet computer 66, mobile phone 64, or Qualcomm 2net system 62 (as per arrow 72), each of which forwards this information to the body-worn sensor (as per arrow 74). Here, the Bluetooth® transceivers within the external wireless device 58, floormat 100, and body-worn sensor 25 are all paired beforehand.

Figure 3:
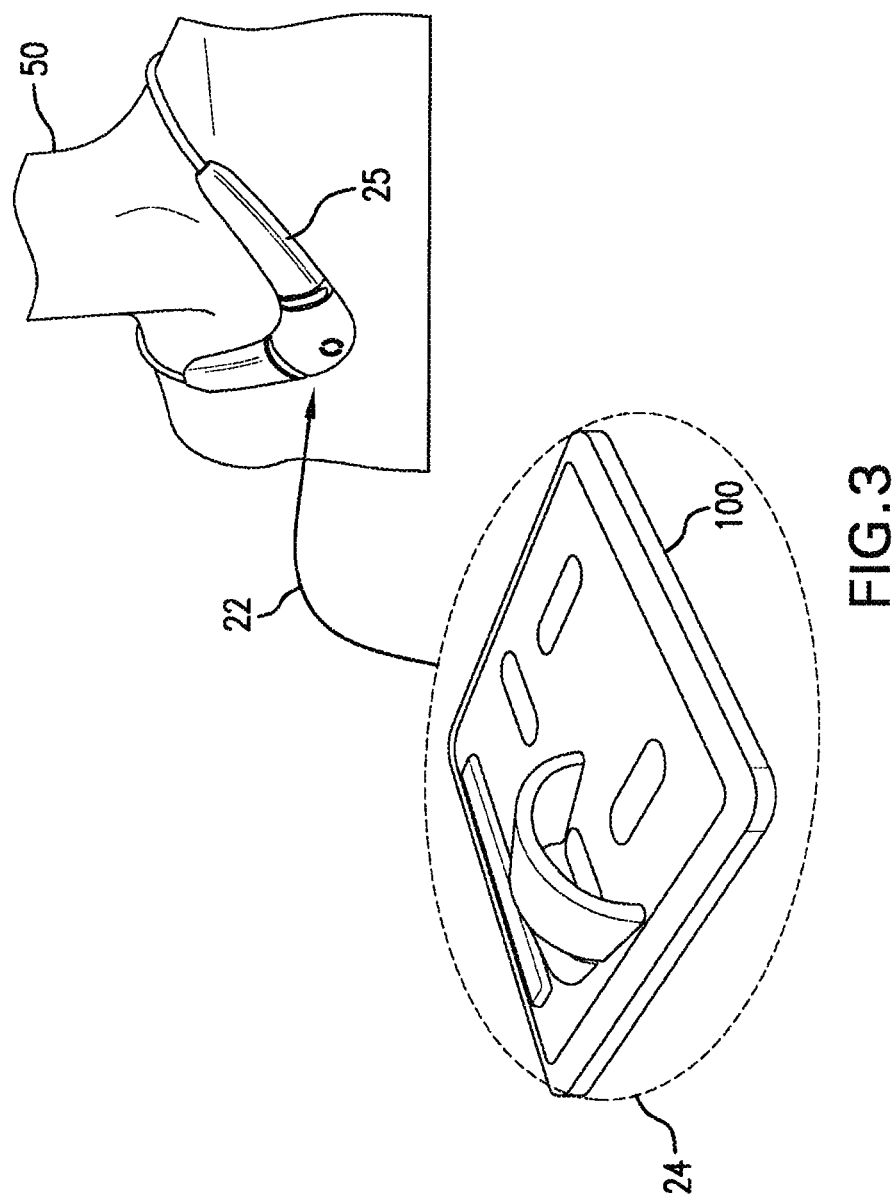
FIG. 3 is a three-dimensional view of the floormat and its weight-measuring system communicating directly with the necklace-shaped sensor.
Figure 5:
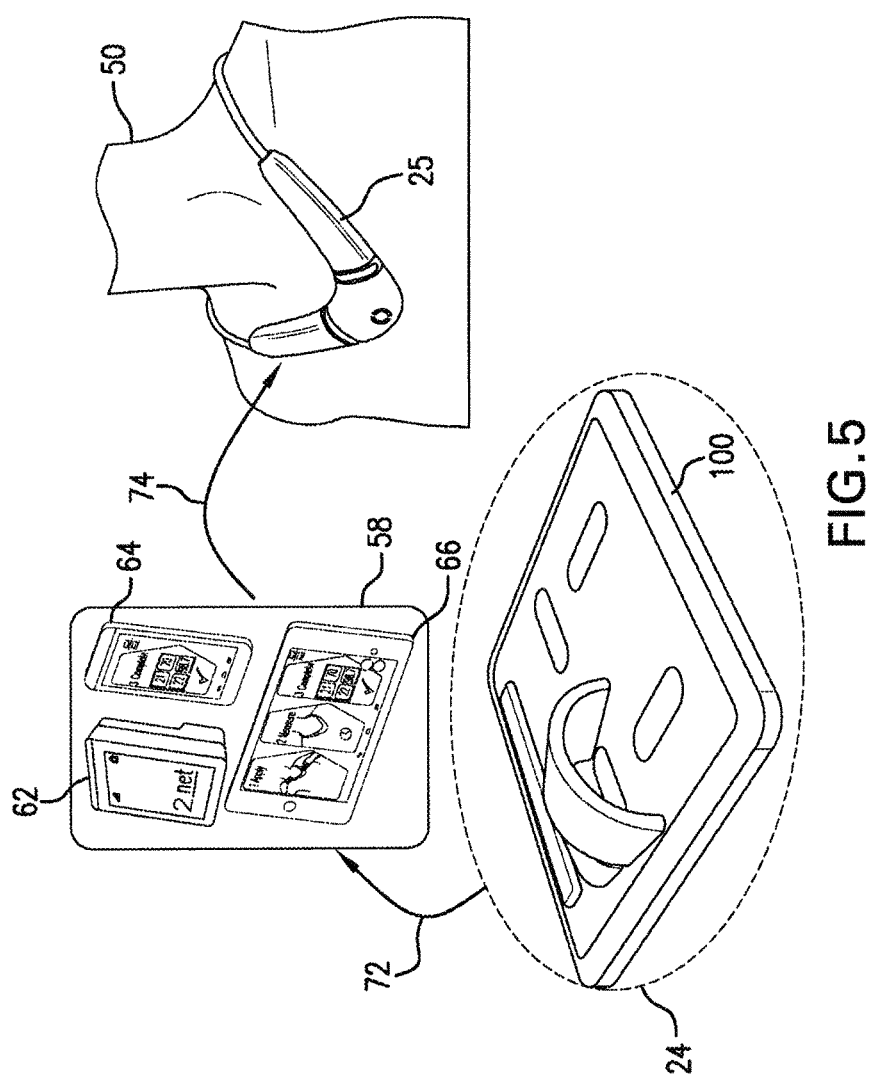
FIG. 5 is a three-dimensional view of the floormat and its weight-measuring system communicating through a wireless gateway with the necklace-shaped sensor.
Figure 6A:
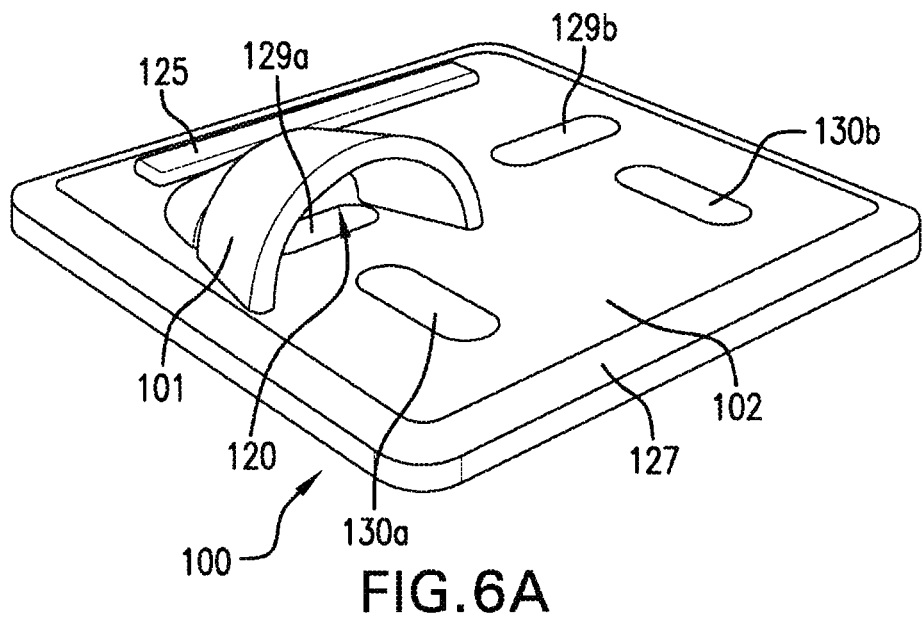
FIG. 6A is a rear perspective view of the floormat shown in FIG. 1.
Figure 6B:
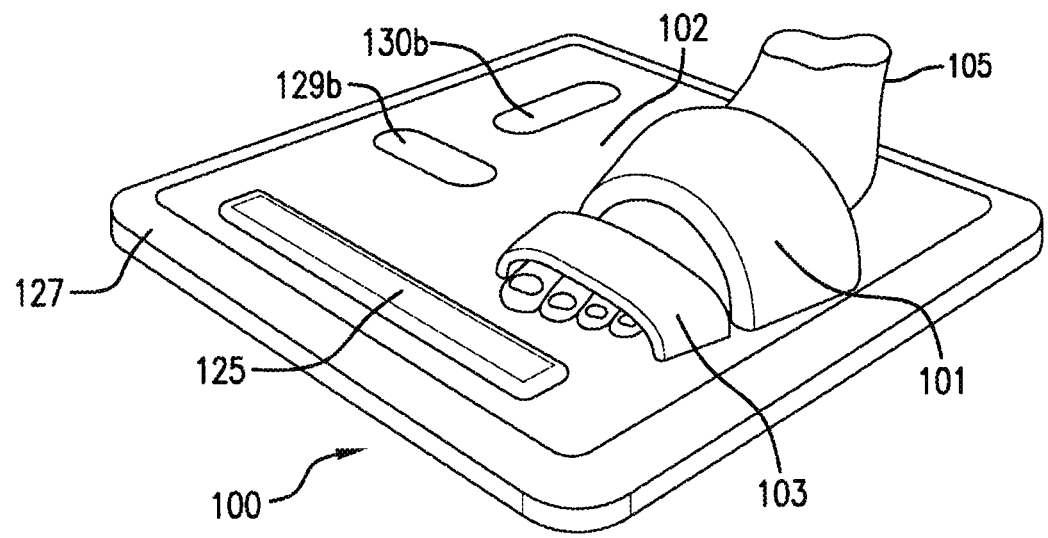
FIG. 6B is a front perspective view of the floormat shown in FIG. 1.

FIGS. 3 and 5 depict similar interactions between the external wireless device 58, floormat 100, and body-worn sensor 25 for the SV calibration. Here, the floormat 100 measures parameters used for the calibration with a weight-measuring system that features a collection of strain gauges and amplifiers, along with bioimpedance and bioreactance systems, all of which are described in more detail below.

The SV calibration includes values of weight and body composition, as measured by the floormat. Body composition can include mass associated with body fat and fluids, fat-free mass, fluid levels, and absolute percentages (normalized by weight) of these parameters. Typically body composition is measured through a combination of bioimpedance and bioreactance, as is described in detail below. Collectively weight and body composition are processed to generate a parameter called a 'volume conductor' ($V_c$) that is used along with parameters extracted from time-dependent waveforms measured using bioimpedance and/or bioreactance circuitry within the body-worn sensor, as described in more detail below. Such parameters include $(\Delta Z(t)/dt)_{max}$, $Z_0$, and left ventricular ejection time (LVET). More specifically, the body-worn sensor processes these parameters using Eq. 7, below:

$$SV = V_c \times \frac{(d\Delta Z(t)/dt)_{max}}{Z_o} \times LVET \quad (7)$$

or, alternatively, Eq. 8, below:

$$SV = V_c \times \sqrt{\frac{(d\Delta Z(t)/dt)_{max}}{Z_o}} \times LVET \quad (8)$$

The BP calibration is calculated for both SYS and DIA, and includes a patient-specific slope ($m_{SYS}$, $m_{DIA}$) relating transit times to changes in blood pressure, and an initial value of SYS and DIA ($SYS_{init}$, $DIA_{init}$). The floormat measures both the patient-specific slopes and the initial blood pressure values. $SYS_{init}$ and $DIA_{init}$ are measured using a version of oscillometry, conducted at the foot. This involves applying a pressure with the cuff-based system to the left foot, and then using a pressure-measuring system to measure pressure-dependent, heartbeat-induced pulsations that are generated by arteries within the foot. More specifically, when the cuff-based system is applied to the foot, blood flowing through the arteries causes pulsations that can be detected as the pressure is decreased from a pressure above SYS to one below DIA. Typically the amplitude of the pulsations, when plotted against the applied pressure, yields a bell-shaped curve that can be processed to determine SYS (which is located on the high-pressure side of the curve), DIA (located on the low-pressure side of the curve), and MAP (the maximum value of the curve). Blood pressures at the feet may be different from those near the bicep, which is where oscillometric measurements are typically made. Thus a correction factor, e.g. one related to the user's height or determined empirically, may be used.

$m_{sys}$ and $m_{dia}$ are slopes that relate changes in blood pressure to pulse transit times, e.g. PAT, PTT, and VTT, as described above. Ideally they are measured by collecting transit times at different blood pressure values. For the invention described herein, this is most easily done with a database in the floormat's memory that stores transit times (measured by the body-worn sensor while the user is standing on the floormat) and cuff-based blood pressure values (measured by the floormat). The measurements stored in the database can be fit with a mathematical function (e.g. a linear equation) to determine a slope that relates changes in blood pressure to changes in transit time. Alternatively, $m_{sys}$ and $m_{dia}$ can be determined during a pressure-dependent measurement using a technique described in the following patent application, the contents of which are incorporated herein by reference: U.S. Patent Application 2014/0236031 to Banet et al., filed Feb. 19, 2014. The patient-specific slopes can also be determined using pre-determined values from a clinical study, and then combining these measurements with biometric parameters (e.g. age, gender, height, weight) collected during the clinical study.

Once the above-described $m_{sys}$, $m_{dia}$, $SYS_{init}$, and $DIA_{init}$ (i.e. the BP calibrations) are determined, they are sent to the body-worn sensor as described above, and then used to make one-time or time-dependent measurements of blood pressure. More specifically, transit times (below, we use PAT, although PTT and VTT could also be used in these equations) correlate inversely to SYS and DIA, as shown below in Eqs. 9 and 10. Without the calibration, PAT only indicates relative changes in SYS and DIA. With the BP calibration, the equations yield both the patient's immediate values of SYS and DIA.

$$SYS = \frac{m_{SYS}}{PAT} + SYS_{cal} \quad (9)$$

$$DIA = \frac{m_{DIA}}{PAT} + DIA_{cal} \quad (10)$$

Typically PAT and SYS correlate better than PAT and DIA, and thus this parameter is first determined using Eq. 9. In one embodiment, DIA is then determined using Eq. 10. Alternatively, PP can be estimated from SV, as described below, and then used with SYS to determine DIA (as described in Eqs. 11 and 12, below). More specifically, PP can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET) to each other. The slope can be estimated from a universal model that, in turn, is determined using a population study. Alternatively, a slope tailored to the individual patient can be used. Such a slope can be selected, for example, using biometric information from a set of patients having known physiological signals.

Figure 7:
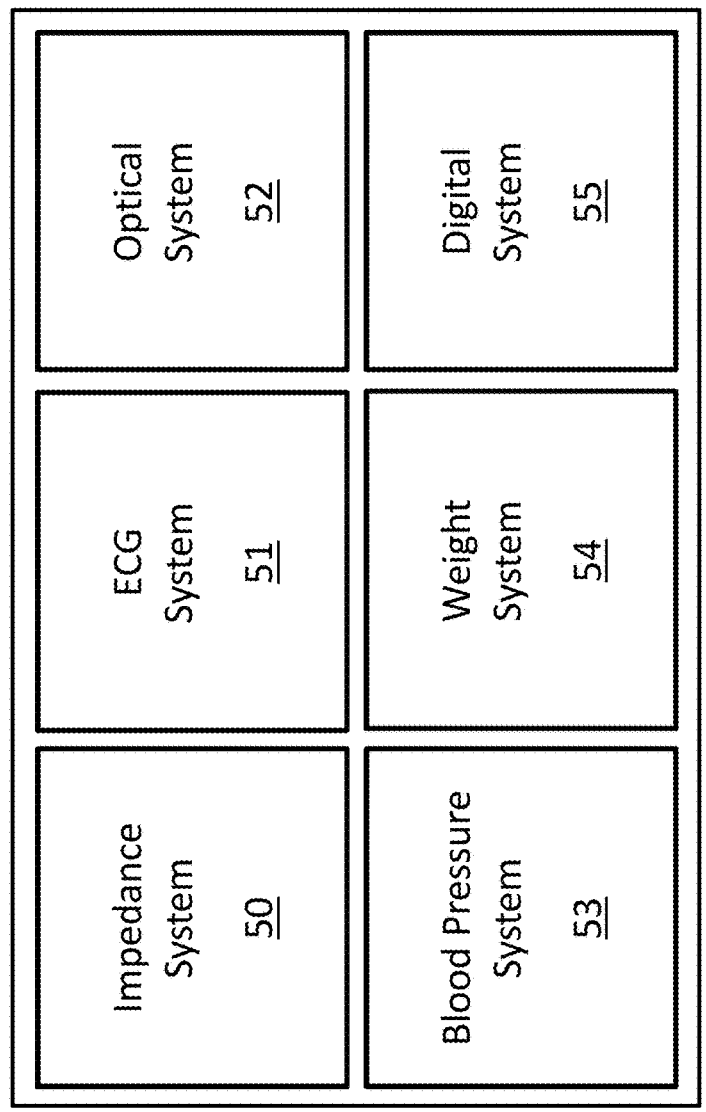
FIG. 7 is a schematic diagram illustrating various sensor subsystems included in the floormat and body-worn systems shown in FIGS. 6A and 6B.

As illustrated in FIG. 7, the floormat 100 includes the following features or subsystems for characterizing the patient: i) an impedance system 50; ii) an ECG system 51; iii) an optical system 52; iv) a blood pressure system 53; v) a weight system 54; and vi) a digital processing system 55. Together, these systems measure and process the above-described physiological information and send it to the mobile device and cloud-based analytics platform for further analysis. These systems 50-55 are integrated within the floormat 100, which provides a simple, easy-to-use device that resembles a conventional weight-measuring scale.

More particularly, the blood pressure system 53 includes back and front straps 101, 103 that form a pocket to receive, for example, the patient's left foot. In other embodiments, however, the straps could be positioned to form a pocket to receive the patient's right foot instead. The straps 101, 103 resemble those present in conventional sandals or bathroom slippers. The back strap 101 includes an inflatable air bladder, described in more detail below, which is coupled to a pressure-delivery system 115. During a measurement, the air bladder and hence the strap 101 inflates and gently constricts blood flow in the patient's foot.

An optical system 120 is housed within or mounted to the front strap 103 in position to face the upper surface of the patient's foot when the patient places his or her foot into the pocket formed by the straps. The optical system 120 measures blood flow and corresponding PPG waveforms from the left foot while pressure is being applied to it, and in this way provides inputs that are used in the blood pressure analysis, as is described in more detail below.

An upper, top layer of material 102, which is suitably composed of silicone rubber, provides a soft, comfortable, non-slip surface for the patient to stand on. The soft, silicone top layer 102 extends over most of the top surface of the floormat 100 and supports the patient's left 105a and right 105b feet during a measurement. Rigid side panels 127, which may be part of a surrounding framework that forms a base for the floormat 100, surround the top surface 102 and help stabilize the floormat 100 when the patient 105 stands on it. The base, of course, should be strong enough to support the weight of an adult patient, e.g., someone weighing up to 350 pounds (or more, perhaps, for use in more clinical healthcare facilities such as obesity-treatment centers). Four support posts (two of which 104a, 104b are shown in the figure) extend from a bottom surface 106 of the floormat, allowing the floormat 100 to rest on a horizontal surface, e.g. a floor. Suitably, the support posts are individually adjustable, e.g., by screwing or unscrewing them into or out of the bottom surface 106 of the floormat 100, so as to level the floormat 100.

A conventional weight-measurement system that uses a Wheatstone Bridge, illustrated and described below in connection with FIG. 10, is located beneath the top layer 102. The weight-measurement system measures signal inputs from strain gauges within the floormat, described in more detail below, to determine the patient's weight.

Four conductive stainless steel electrodes 129a, 129b, 130a, 130b are partially embedded within the top layer of material 102, with upper surfaces of the electrodes exposed so as to make contact with the soles of the patient's feet when the patient stands on the floormat. The electrodes are used to measure electrical signals from the patient's left and right feet simultaneously, which signals are amplified and filtered by circuits on the circuit board 117 to generate BI and ECG waveforms as well as bioreactance impedance signals, the latter of which are used to determine percent body fat and muscle mass. (BI is an impedance waveform that is analogous to TBI, except it is not obtained exclusively from the patient's chest, and therefore does not reference the thorax via a "T" in its acronym.) While stainless steel is a preferred material for the electrodes, other materials may also be used. These include conductive rubber, conductive fabrics, metals other than stainless steel, and materials coated with conductive materials, such as films of Ag/AgCl.

An electronics module 125, which may be housed within a forward portion of the top layer 102, includes all of the electronics for the impedance 50, ECG 51, optical 52, blood pressure 53, weight 54, and digital 55 systems. These systems generally include a number of analog amplifiers and filters, which are described in detail in the following co-pending patent applications entitled "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Aug. 21, 2014; and "BODY-WORN SENSOR FOR CHARACTERIZING PATIENTS WITH HEART FAILURE," U.S. Ser. No. 14/145,253, filed Jul. 3, 2014, all three of which were incorporated by reference above. The digital processing system 55 within the electronics module 125 digitizes the analog waveforms generated by impedance 50, ECG 51, optical 52, blood pressure 53, and weight 54 systems, and then processes the digitized waveforms using a number of algorithms operating on a microprocessor, as is described in more detail below.

Figure 8A:
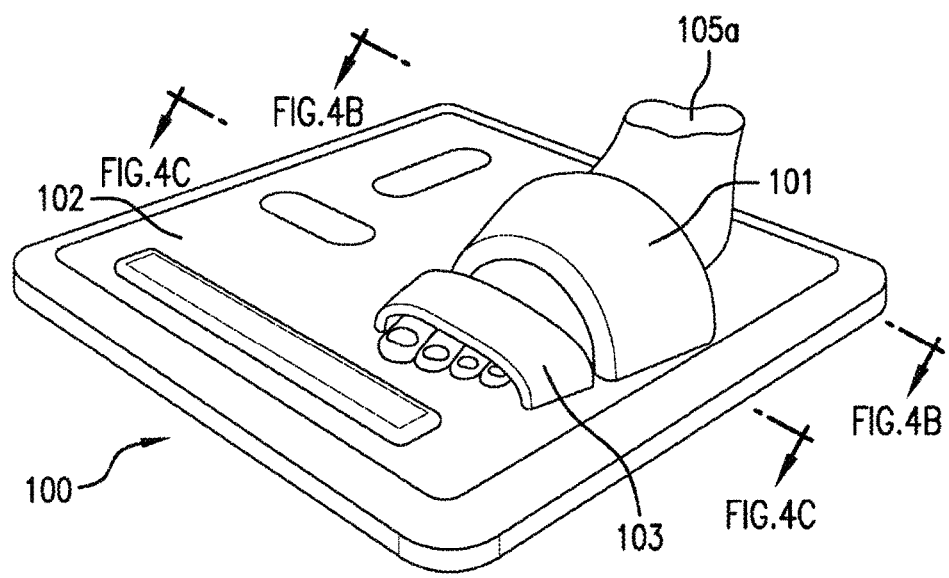
FIG. 8A is a front perspective view of the floormat shown in FIG. 6B.
Figure 8B:
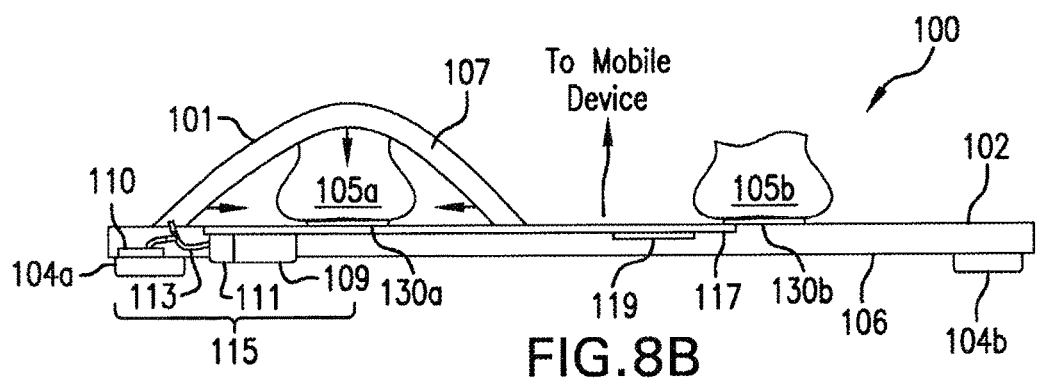
FIG. 8B is a schematic section view along sight-line 8B in FIG. 8A.
Figure 8C:
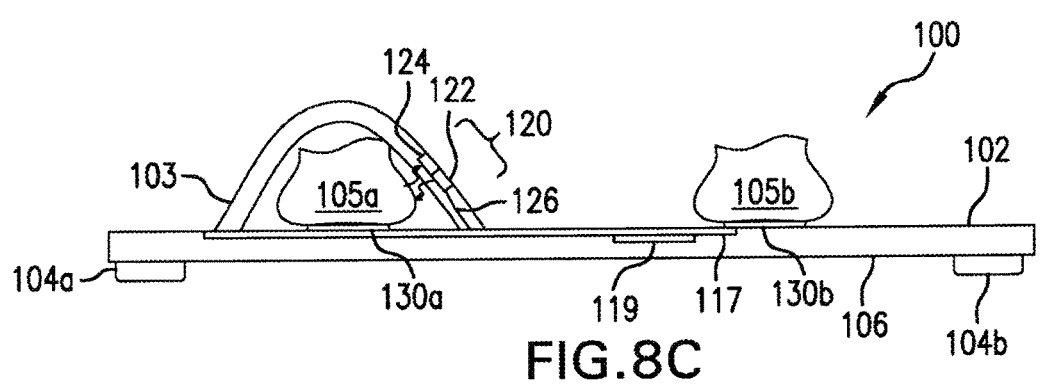
FIG. 8C is a schematic section view along sight-line 8C in FIG. 8A.

FIGS. 8A-C respectively show a three-dimensional perspective view of the floormat 100 with a patient standing on it. Section views (FIGS. 8B, 8C) better illustrate the back strap 101 and the front strap 103, which cover corresponding portions of the patient's left foot 105a when the patient is using the floormat 100 to measure his or her various physiological parameters.

To measure blood pressure (e.g. SYS and DIA), a diaphragm pump 109 pumps air through a controllable valve 111 and into bladder 107 via a flexible tube 113. The bladder 107 may be provided as a separate bladder "bag" that fits within a pocket in the back strap 101, or it may be formed simply as an airtight chamber within the back strap 101 itself. A pressure sensor 110 that is in fluid (i.e., air) communication with the flexible tube 113 senses pressure within the bladder 107. Collectively, the pump 109, valve 111, and flexible tube 113 form a pressure-delivery system 115 that pumps air into the inflatable bladder 107, thereby causing it to constrict around the patient's left foot 105a; after air inside the bladder reaches a pre-determined pressure, the valve 111 slowly releases pressure. During inflation or deflation, the pressure sensor 110 measures the resultant pressure within the system.

A circuit board 117 with a programmable microprocessor 119 controls operation of the pressure-delivery system 115. Typically, such "control" means switching on and off a transistor (e.g. a field-effect transistor, or FET, not shown in the figure), which causes a voltage (e.g. 5V) to be provided to or removed from the pump 109 and valve 111. Such voltage opens the valve 111 and powers the pump 109, thereby causing it to pump air through the flexible tube 113 and into the bladder 107 to cause the bladder to expand. As the bladder 107 expands, the space inside the rear strap 101 contracts around the bridge of the patient's left foot, thereby constricting blood flow (which is a requirement for measuring blood pressure in this manner, as described in more detail below).

The front strap 103, on the other hand, is positioned to cover a front portion of the patient's left foot 105a and includes the above-referenced optical system 120. The optical system 120 includes a light source 122 and a photodetector 124 that are used to generate a PPG waveform from the top of the patient's foot. The light source 122 may be a light-emitting diode (LED), and the photodetector may be a standard PIN photodetector. During a measurement, the light source 122 emits optical radiation, alternating between red (about 660 nm) and infrared (about 905 nm) wavelengths, to irradiate blood vessels in the front portion of the left foot 105a. Typically with such systems, the radiation propagates a few hundred microns into blood vessels on the foot's outer surface, where it irradiates the vessels and partially reflects back towards the photodetector.

As dictated by Beer's law, which describes the basic premise of optical absorption through a volumetric sample, the reflected radiation will vary in intensity as blood pulses through the vessels and causes them to expand and contract periodically, thus causing the reflected radiation's intensity to modulate. The reflected radiation, in turn, irradiates the photodetector 124, which, in response to the sensed reflected radiation, generates a proportional, modulated photo-induced current that passes through a thin cable 126 to the circuit board 117, where it is amplified and filtered to generate the PPG waveform.

With the physical structure of the floormat 100 in mind, its methods to acquire and process the pressure, PPG, BI, and ECG waveforms, and thereby determine vital signs and hemodynamic parameters, are described in more detail below.

2. Blood Pressure Measurement

To measure blood pressure, the pressure-delivery system and the optical system simultaneously measure pressure and blood pulsation and generate time-dependent pressure and PPG waveforms 150, 152 as illustrated in FIGS. 9B and 9C, respectively. These waveforms can be analyzed as the bladder deflates, as is illustrated in the figures. In this case, the optical pulsation in the PPG waveform gradually reappears as the pressure drops below SYS. Alternatively, the waveforms can be measured as the bladder inflates. Here, the pulsation in the waveform gradually diminishes as the pressure approaches SYS. In either case, the microprocessor processes these waveforms with a mathematical model to identify a specific pressure corresponding to the disappearance-point (or reappearance-point) of heartbeat-induced pulsation in the PPG waveform 152.

More specifically, the model assumes that pressure applied by the bladder compresses the arteries in the patient's foot, thereby at least partially occluding blood flow in the arteries. This, in turn, causes the heartbeat-induced pulsation in the PPG waveform to gradually decrease in amplitude during pressurization of the bladder until it (the pulsation) eventually becomes undetectable or, alternatively, to increase in amplitude (if measurement is made during depressurization of the bladder) until it becomes detectable. The pressure being applied to the patient's foot at the moment when pulsation reappears or disappears, as the case may be, corresponds to SYS. A conventional peak-detecting algorithm executing on the microprocessor can be used to detect the onset or cessation of the pulse amplitude in the PPG waveform to identify this "breakpoint;" correlating the breakpoint with the pressure waveform 150 allows the system to make a direct measurement of SYS.

Alternatively, a "fitting" algorithm can be used to model the systematic decrease in pulse amplitude with applied pressure with a mathematical function (e.g. a linear or polynomial function) featuring parameters that are iteratively varied, with the parameters providing the closest approximation to the measured PPG waveform being used to estimate SYS. This latter technique may be used to estimate SYS fairly quickly.

In still other alternative embodiments, pulsations in the pressure waveform caused by heartbeat-induced blood flow in the patient's foot can be analyzed as is done in conventional oscillometry (i.e. the standard technique for automated blood pressure-monitoring systems). Typically, in this case, algorithms process the pressure-dependent amplitude in the pulsations, which are extracted from the pressure waveform with hardware or software filters to remove the DC background. This typically results in a bell-shaped curve from which MAP (corresponding to the curve's maximum point), DIA (extracted from the relatively low-pressure side of the curve), and SYS (extracted from the relatively high-pressure side of the curve) are determined.

Referring back to FIG. 9, when pressure applied by the air bladder is roughly equal to the mean pressure within the underlying blood vessel—a condition that causes the heartbeat-induced pulsations to distort the vessels so that their volumetric change is maximized—the pulse amplitude will be maximized. This maximization of the pulse amplitude can, in turn, be detected and therefore used to approximate MAP. Subsequently, DIA is calculated from SYS, MAP (as so approximated), and pulse pressure (PP) using to Eqs. 11 and 12, below.

$$MAP \approx DIA + \frac{1}{3} \times PP \quad (11)$$

$$PP = SYS - DIA \quad (12)$$

Suitable circuits 160 and 170 to control operation of the pressure-delivery system and the optical system, which work together to measure blood pressure as described above, are illustrated in FIGS. 10B and 10C, respectively.

3. Stroke Volume, Cardiac Output, and Fluid Measurements

Figure 12D:
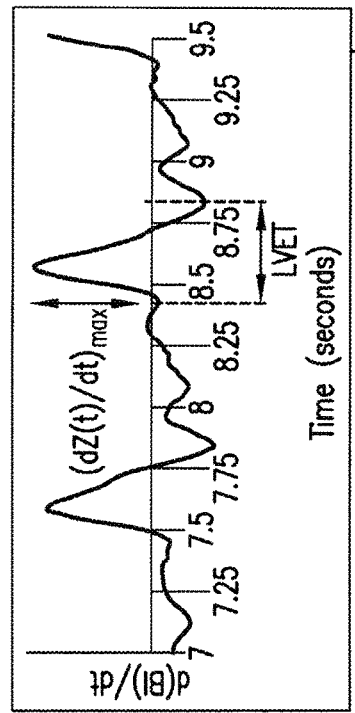
FIG. 12D is a time-dependent plot showing a derivative of the BI waveform shown in FIG. 12C.
Figure 12A:
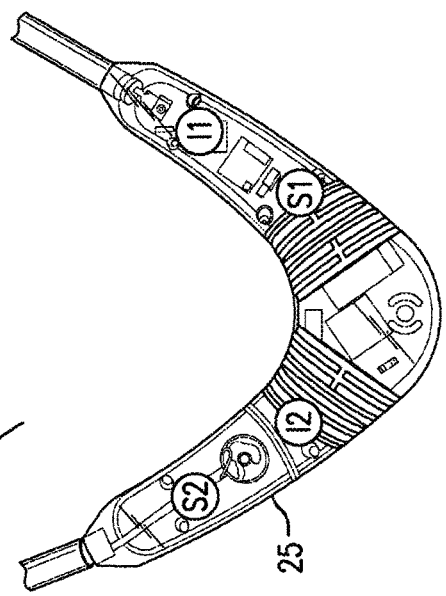
FIG. 12A is a rear perspective view of the floormat shown in FIG. 6A.
Figure 12C:
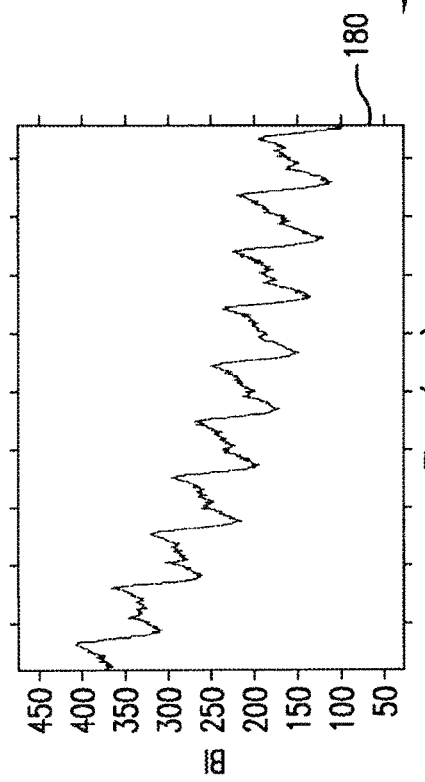
FIG. 12C is a time-dependent plot showing a bioimpedance (BI) waveform generated with the necklace-shaped sensor of FIG. 12A.
Figure 12B:
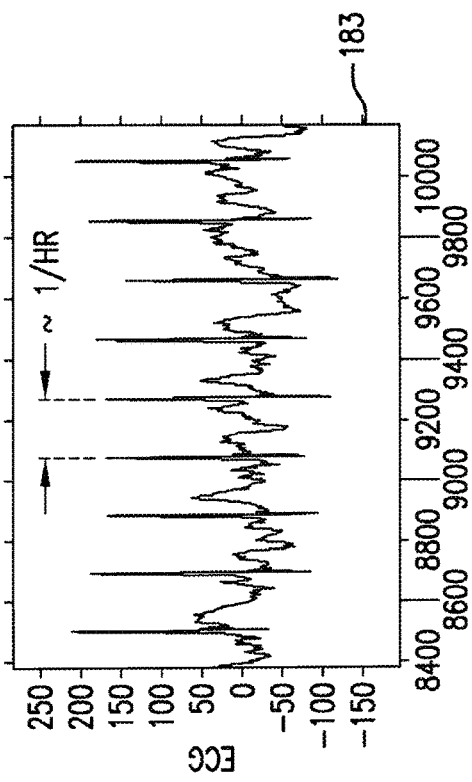
FIG. 12B is a time-dependent plot showing an ECG waveform generated with the necklace-shaped sensor of FIG. 12A.

FIG. 12A shows a body-worn sensor 25 for measuring SV and CO. As indicated schematically in the figure, the sensor 25 includes a pair of current-injecting electrode regions I1, I2 described in detail below. (It should be noted that during a measurement, an electrode patch attaches to the electrode-retaining magnets on both lateral sides of the sensor 25.) The sensor 25 also includes a pair of voltage-sensing electrode regions S1, S2. During a measurement, the S1, S2 regions sense bioelectric signals. These pass through a first circuit, which includes a collection of filters, amplifiers, and rectifying components that generate a time-dependent, analog TBI waveform that relates by Ohm's Law to impedance encountered by the injected current. FIG. 12C shows a representative BI waveform resulting from this process. Likewise, the bioelectric signals also pass through a second circuit, which features a differential amplifier and filtering components that generate a time-dependent, analog ECG waveform, as shown in FIG. 12B.

Thus, to use the sensor 25 to monitor a patient's physiology, a pair of 2-part electrode patches are first attached to the electrode regions I1, I2, S1, S2, and then the electrodes are attached to the patient's chest as noted above. Ideally, each electrode patch attaches just below the patient's collarbone, near the patient's left and right arms. During a measurement, the impedance circuit (described more fully below) injects a high-frequency, low-amperage current (I) into the patient's skin through electrode regions I1, I2. Typically, the modulation frequency is about 70 kHz, and the current is about 6 mA. The current injected by each electrode region I1, I2 is out of phase by 180° with respect to the other. It encounters static (i.e. time-independent) resistance from components such as fluids and, to a lesser extent, bone, skin, and other tissue in the patient's chest. Additionally, blood and other fluids in the chest conduct the current to some extent. Blood ejected from the left ventricle of the heart into the aorta provides a dynamic (i.e. time-dependent) resistance. As the largest artery passing blood out of the heart, the aorta has a dominant impact on the dynamic resistance; other vessels such as the superior vena cava, on the other hand, will contribute to the dynamic resistance in a minimal way.

Electrode regions S1, S2 measure a time-dependent voltage (V) that varies with resistance (R) encountered by the injected current (I) according to Ohm's Law, shown below in Equation 13:

$$V = I \times R \quad (13)$$

During a measurement, the time-dependent voltage sensed by the forward electrodes is amplified and filtered by an impedance circuit and ultimately processed with an analog-to-digital converter in the electronics module.

Two further waveforms can be extracted from the BI waveform. The first waveform 180 (FIG. 12C) exhibits relatively high-frequency variations caused by heartbeat-induced impedance changes measured by the BI system. This represents the AC component of the BI bioimpedance waveform. Furthermore, the mathematical derivative of the AC component of the BI waveform (plot 182, FIG. 12D) can be processed with a first algorithm to determine $(dZ(t)/d(t))_{max}$ and left ventricular ejection time (LVET). (As used herein, $d(Z(t))/dt$ and $d(BI(t)/d(t)$ are considered to be equivalent.) A separate waveform—not shown in the figure but exhibiting relatively low-frequency variations in impedance—can be processed with a second algorithm to determine $Z_0$. These three parameters—$(dZ(t)/d(t))_{max}$, LVET, and $Z_0$—are then processed to calculate SV using an equation such as that shown in Eq. 14, which is Sramek-Bernstein equation, or a mathematical variation thereof.

$$SV = \delta \frac{L^3}{4.25} \frac{(dZ(t)/dt)_{max}}{Z_0} LVET \quad (14)$$

In Eq. 14, the term "Z(t)" represents the AC component of a conventional impedance waveform. According to the invention described herein, Z(t) is replaced with the AC component of the BI waveform. δ represents compensation for body mass index, which may be determined using the floormat's weight scale component, as described in more detail below. $Z_0$ is a base impedance value estimated from the DC component of the BI waveform. L is estimated from the distance separating respective current-injecting and voltage-measuring electrodes, and can be approximated from the patient's height.

Alternatively, waveforms measured with the impedance system can be processed with an algorithm based on Eqs. 7 and 8, above.

Typically, a high resistance (e.g. one above about 30Ω) indicates a dry, dehydrated state. In that case, the lack of conducting thoracic fluids increases resistivity in the patient's chest. Conversely, a low resistance (e.g. one below about 19Ω) indicates the patient has more thoracic fluids, and is possibly overhydrated. In that case, the abundance of conducting thoracic fluids decreases resistivity in the patient's chest. LVET can be determined from the TBI waveform as described above with reference to FIG. 12D, or from the HR using an equation called "Weissler's Regression," shown below in Equation 15, that estimates LVET from HR:

$$LVET = -0.0017 \times HR + 0.413 \quad (15)$$

Weissler's Regression allows LVET to be estimated from HR determined from the ECG waveform. This equation and several mathematical derivatives are described in detail in the following reference, the contents of which are incorporated herein by reference: "*Impedance Cardiography, Pulsatile blood flow and the biophysical and electrodynamic basis for the stroke volume equations*," Bernstein, Journal of Electrical Bioimpedance, Vol. 1, p. 2-17, 2010. Both the Sramek-Bernstein Equation and an earlier derivative of this, called the Kubicek Equation, feature a "static component," $Z_0$, and a "dynamic component," Z(t), the derivative of which relates to LVET and a $(dZ/dt)_{max}/Z_0$ value. These equations assume that $(dZ(t)/dt)_{max}/Z_0$ represents a radial velocity of blood (with units of Ω/s) due to volume expansion of the aorta.

5. Pulse Transit Time Measurements

Pulse transit times are timing-related parameters that can be extracted from the physiological waveforms described above. They are known to correlate inversely to blood pressure and, additionally, may indicate the compliance (and thus stiffness) of the patient's arteries. In certain embodiments, the floormat can measure pulse transit times, as explained in more detail below, and then use these parameters to estimate blood pressure without using a pressure-delivery system like the one described above. Additionally, pulse transit times, combined with blood pressure values determined using the pressure-delivery system, may be used to estimate changes in the patient's arterial compliance. One technique for making such an estimation is described in detail in the following reference, the contents of which are incorporated herein by reference: "Vital sign monitor for cufflessly measuring blood pressure corrected for vascular index," Publication number WO2008154647, filed Jun. 12, 2008.

Figure 14:
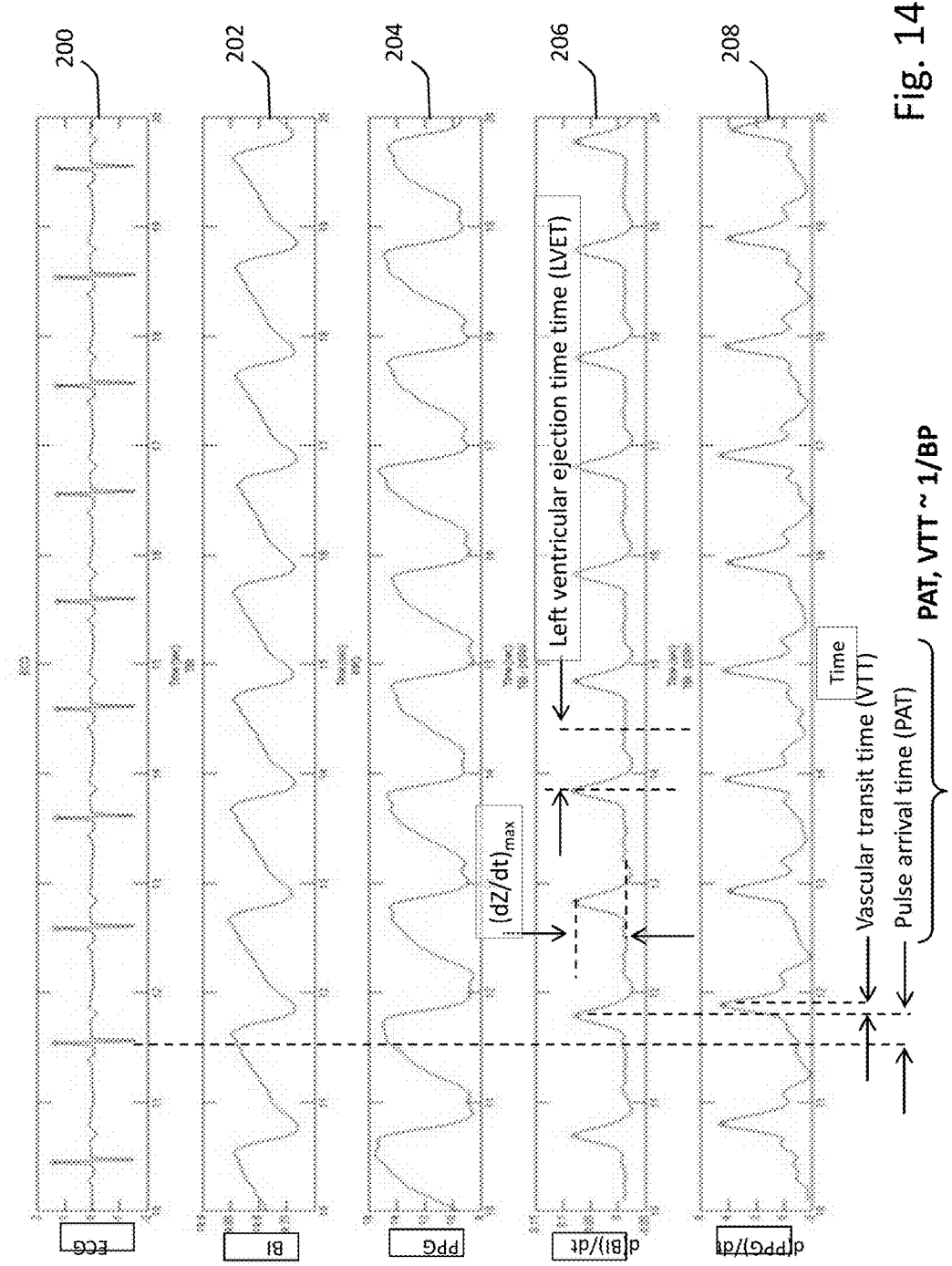
FIG. 14 is a set of time-dependent graphs showing (from top to bottom) ECG, BI, PPG, d(BI)/dt, and d(PPG)/dt waveforms.

FIG. 14, for example, shows the following time-dependent waveforms, as measured by the body-worn sensor: ECG (plot 200), BI (plot 202), PPG (plot 204), d(BI)/dt (plot 206), and d(PPG)/dt (plot 208). As shown in plots 200 and 202, individual heartbeats produce time-dependent pulses in both the ECG and BI waveforms. As is clear from the data, pulses in the ECG waveform precede those in the BI waveform. The ECG pulses—each featuring a sharp, rapidly rising QRS complex—indicate initial electrical activity in contractions in the patient's heart and, informally, the beginning of the cardiac cycle.

BI pulses follow the QRS complex by about 100 ms and indicate blood flow through arteries in the region of the body where the electrodes make contact with the skin. During a heartbeat, blood flows from the patient's left ventricle into the aorta; the volume of blood that leaves the ventricle is the SV. Blood flow periodically enlarges this vessel, which is typically very flexible, and also temporarily aligns blood cells (called erythrocytes) from their normally random orientation. Both the temporary enlargement of the vessel and alignment of the erythrocytes improves blood-based electrical conduction, thus decreasing the electrical impedance as measured with BI. The d(BI)/dt waveform (plot 206) shown in FIG. 14 is a first mathematical derivative of the raw BI waveform, meaning its peak represents the point of maximum impedance change.

A variety of time-dependent parameters can be extracted from the ECG and BI waveforms. For example, it is well know that HR can be determined from the time separating neighboring ECG QRS complexes. Likewise, LVET can be measured directly from the derivative of the BI pulse, as shown in FIG. 12D, and is determined from the onset of the derivatized pulse to the first positive-going zero crossing. Also measured from the derivatized BI pulse is $(dBI/dt)_{max}$, which is a parameter used to calculate SV as described above.

The time difference between the ECG QRS complex and the peak of the derivatized BI waveform represents a pulse arrival time PAT, as indicated in FIG. 14. This value can be calculated from other fiducial points, including, in particular, locations on the BI waveform such as the base, midway point, or maximum of the heartbeat-induced pulse. Typically, the maximum of the derivatized waveform is used to calculate PAT, as it is relatively easy to develop a software beat-picking algorithm that finds this fiducial point.

PAT correlates inversely to SYS and DIA, as shown below in Eqs. 16 and 17, where $m_{SYS}$ and $m_{DIA}$ are patient-specific slopes for SYS and DIA, respectively, and $SYS_{cal}$ and $DIA_{cal}$ are values of SYS and DIA, respectively, measured during a calibration measurement. (Such a measurement can, for example, be performed with the pressure-delivery and optical systems described above.) Without the calibration, PAT only indicates relative changes in SYS and DIA. The calibration yields both the patient's immediate values of SYS and DIA. Multiple values of PAT and blood pressure can be collected and analyzed to determine patient-specific slopes $m_{SYS}$ and $m_{DIA}$, which relate changes in PAT with changes in SYS and DIA. The patient-specific slopes can also be determined using pre-determined values from a clinical study, and then combining these measurements with biometric parameters (e.g. age, gender, height, weight) collected during the clinical study.

$$SYS = \frac{m_{SYS}}{PAT} + SYS_{cal} \quad (16)$$

$$DIA = \frac{m_{DIA}}{PAT} + DIA_{cal} \quad (17)$$

In embodiments of the invention, waveforms like those shown in FIG. 14 can be measured and processed with the body-worn sensor to determine PAT. This parameter, combined with a calibration determined as described above, can be used by the floormat to determine blood pressure without a physical-pressure-applying mechanism via Eqs. 16 and 17, above. Typically PAT and SYS correlate better than PAT and DIA, and thus this parameter is first determined using Eq. 16. In one embodiment, DIA is then determined using Eq. 17. Alternatively, PP can be estimated from SV, as described below, and then used with SYS to determine DIA according to, e.g. Eqs. 7 and/or 8, above.

PP can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET) to each other. The slope can be estimated from a universal model that, in turn, is determined using a population study.

Alternatively, a slope tailored to the individual patient can be used. Such a slope can be selected, for example, using biometric parameters describing the patient as described above.

Here, PP/SV slopes corresponding to such biometric parameters are determined from a large population study and then stored in computer memory on the floormat. When a floormat is assigned to a patient, their biometric data is entered into the system, e.g. using a GUI operating on mobile telephone, that transmits the data to a microprocessor in the floormat via Bluetooth®. Then, an algorithm on the floormat processes the data and selects a patient-specific slope. Calculation of PP from SV is explained in the following reference, the contents of which are incorporated herein by reference: "Pressure-Flow Studies in Man. An Evaluation of the Duration of the Phases of Systole," Harley et al., *Journal of Clinical Investigation*, Vol. 48, p. 895-905, 1969. As explained in this reference, the relationship between PP and SV for a given patient typically has a correlation coefficient r that is greater than 0.9, which indicates excellent agreement between these two properties. Similarly, in the above-mentioned reference, SV is shown to correlate with the product of PP and LVET, with most patients showing an r value of greater than 0.93 and the pooled correlation value (i.e., the correlation value for all subjects) being 0.77. This last value indicates that a single linear relationship between PP, SV, and LVET may hold for all patients.

More preferably, PP is determined from SV using relative changes in these values. Typically, the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: "*Pulse pressure variation and stroke volume variation during increased intra-abdominal pressure: an experimental study*," Didier et al., *Critical Care*, Vol. 15:R33, p. 1-9, 2011. Here, the relationship between PP variation and SV variation for 67 subjects displayed a linear correlation of r=0.93, which is an extremely high value for pooled results that indicates a single, linear relationship may hold for all patients.

From such a relationship, PP can be determined from the BI-based SV measurement, and SYS can be determined from PAT. DIA can then be calculated from SYS and PP.

The body-worn sensor determines RR from the DC BI waveform, described above. In this case, the patient's respiratory effort moves air in and out of the lungs, thus changing the impedance in the thoracic cavity. This time-dependent change maps onto the BI waveform, typically in the form of oscillations or pulses that occur at a much lower frequency than the heartbeat-induced cardiac pulses shown in FIG. 12C. Simple signal processing (e.g. filtering, beat-picking) of the low-frequency, breathing-induced pulses in the waveform yields RR.

Another parameter, called vascular transit time (VTT), can be determined from pulsatile components in the BI (or d(BI)/dt) waveform and the PPG (or d(PPG)/dt) waveform. FIG. 14 shows in more detail how VTT is determined. It can be used in place of PAT to determine blood pressure, as described above. Using VTT instead of PAT in this capacity offers certain advantages, namely, lack of signal artifacts such as pre-injection period (PEP) and isovolumic contraction time (ICT), which contribute components to the PAT value but which are not necessarily sensitive to or indicative of blood pressure.

6. Weight, Percent Body Fat, and Muscle Mass Measurement

The floormat also measures biometric parameters such as weight, percentage body fat, and muscle mass (also known as skeletal muscle). Weight is measured using a relatively conventional scale mechanism within the floormat. As illustrated in FIGS. 11A-D, for example, embodiments of the floormat 100 include a stabilizing bar 150 with one or more load cells 148 attached to it to measure the patient's weight. The stabilizing bar 150, which may have holes 154 extending through it (FIG. 11C) to reduce its rigidity and allow it to flex/induce strain when a patient stands on the floormat, is suitably disposed on the floormat's bottom surface and connected to the supporting posts 104a, 104b at its distal ends. In some embodiments of the floormat, the floormat 100 may have two stabilizing bars, with one stabilizing bar (as illustrated) being connected to supporting posts 104a, 104b on one side of the floormat and the other stabilizing bare (not illustrated) being connected to supporting posts (also not illustrated) located at the floormat's opposite corners. In the illustrated embodiment, the two stabilizing bars are parallel to each other; in alternate embodiments of the floormat, they may intersect with each in a criss-cross pattern.

As further illustrated in the figures, load cell 148 is located near the mid-point of the stabilizing bar and is integrated directly into the stabilizing bar, and a pair of strain gauges 151, 152 are connected to opposite surfaces of the stabilizing bar 150 to form the load cell 148 portion of the stabilizing bar. In one embodiment of the floormat, the strain gauges may be flexible circuits with a serpentine pattern of conductive traces having a resistance value that varies with strain. When the patient stands on the floormat, the stabilizing bar flexes or bows; depending on the specific manner in which the stabilizing bar is mounted and supported within the base of the floormat, it will bow either upwardly (concavity-down) or downwardly (concavity-up). With such flexing of the stabilizing bar, the strain gauge located on the "inside" surface of the bow will be compressed, while the strain gauge located on the "outside" surface of the how will be extended. Both compression and extension of the strain gages cause slight changes in the strain gauges' resistance values—one change being a decrease in resistance and the other change being an increase in resistance—and such variation in resistance can be measured and used to determine the amount by which the stabilizing bar flexes and, hence, the weight being applied to it.

In alternate embodiments, the strain gauges shown in FIG. 11 can be disposed in other locations within the floormat. In one alternate configuration, for example, they are disposed in the floormat's support posts 104a, 104b, and configured so that a patient standing on the floormat causes them to compress and extend, as described above.

In total, the illustrated embodiment of a floormat according to the invention has two load cells—one for each stabilizing bar—and thus four strain gauges. As illustrated in FIG. 11D, each of the strain gauges forms an arm of an electrical circuit 160 featuring a four-resistor circuit component (i.e., a Wheatstone Bridge 162) that, when connected to an amplifier circuit 164, can be used to determine the patient's weight.

During a measurement, the patient stands on the top surface 102 of the floormat 100. The force associated with the patient's weight affects the strain gauges, resulting in small resistance changes that are amplified by the Wheatstone Bridge 162, causing it to produce an output voltage. The output voltage is further amplified by the amplifier circuit 164, thus resulting in an input voltage to an analog-to-digital converter that varies with weight. (Gain resistor RG determines the degree of amplification in the amplifier circuit 164.) The system can be calibrated by placing weights of known values on the floormat's surface and then measuring the resulting voltages that are input to the analog-to-digital converter. Once the load-cell system has been calibrated, the floormat can measure the patient's weight.

The floormat complements this weight measurement by estimating the patient's percent body fat and muscle mass. This measurement is implemented with the four stainless steel electrodes 129a, 129b, 130a, and 130b that contact the soles of the patient's feet. More specifically, as addressed above, these electrodes measure electrical signals to generate electrical impedance waveforms $Z_0$ and $\Delta Z(t)$. $Z_0$, in particular, is an input into Eq. 16, below, and is used to determine percentage of body fat. Additionally, the floormat may include another circuit that measures a parameter called bio-reactance (Xc), which is also used as an input in Eq. 16. (Bio-reactance refers to the electrical resistive, capacitive, and inductive properties of blood and biological tissue that induce phase shifts between an applied electrical current and the resulting voltage signal. This parameter is distinguished from bioimpedance, addressed above, which refers to the electrical properties of blood and tissue that determine the amplitude of the voltage field resulting from an applied electrical current.)

During a measurement, the stainless steel electrodes measure electrical signals that are processed with circuitry in the floormat to determine $Z_0$ (from the bioimpedance measurement used to sense BI waveforms) and Xc (from the bioreactance measurement, described above). These parameters are used in Eq. 18, below, along with the patient's weight as measured by the weight-measuring system, to estimate the patient's fat-free mass (FFM), which can be used as an estimate of muscle mass:

$$\text{FFM (kg)} = a \times (\text{height}^2/Z_0) + b \times (\text{weight}) - c \times (\text{age}) + d \times X_c - e \quad (18)$$

where a, b, c, and d are constants determined from a clinical study, as follows: a=0.7374, b=0.1763, c=0.1773, d=0.1198, and e=2.4658. Eq. 18, along with the constants used to estimate FFM, are described in detail in the following reference, the contents of which are incorporated herein by reference: Macias et al., *Body fat measurement by bioelectrical impedance and air displacement plethysmography: a cross-validation study to design bioelectrical impedance equations in Mexican adults*; Nutrition Journal; 6: (2007). Subtracting FFM from body weight, and then dividing this number by the body weight, is used to estimate the patient's percentage of body fat.

Figure 15:
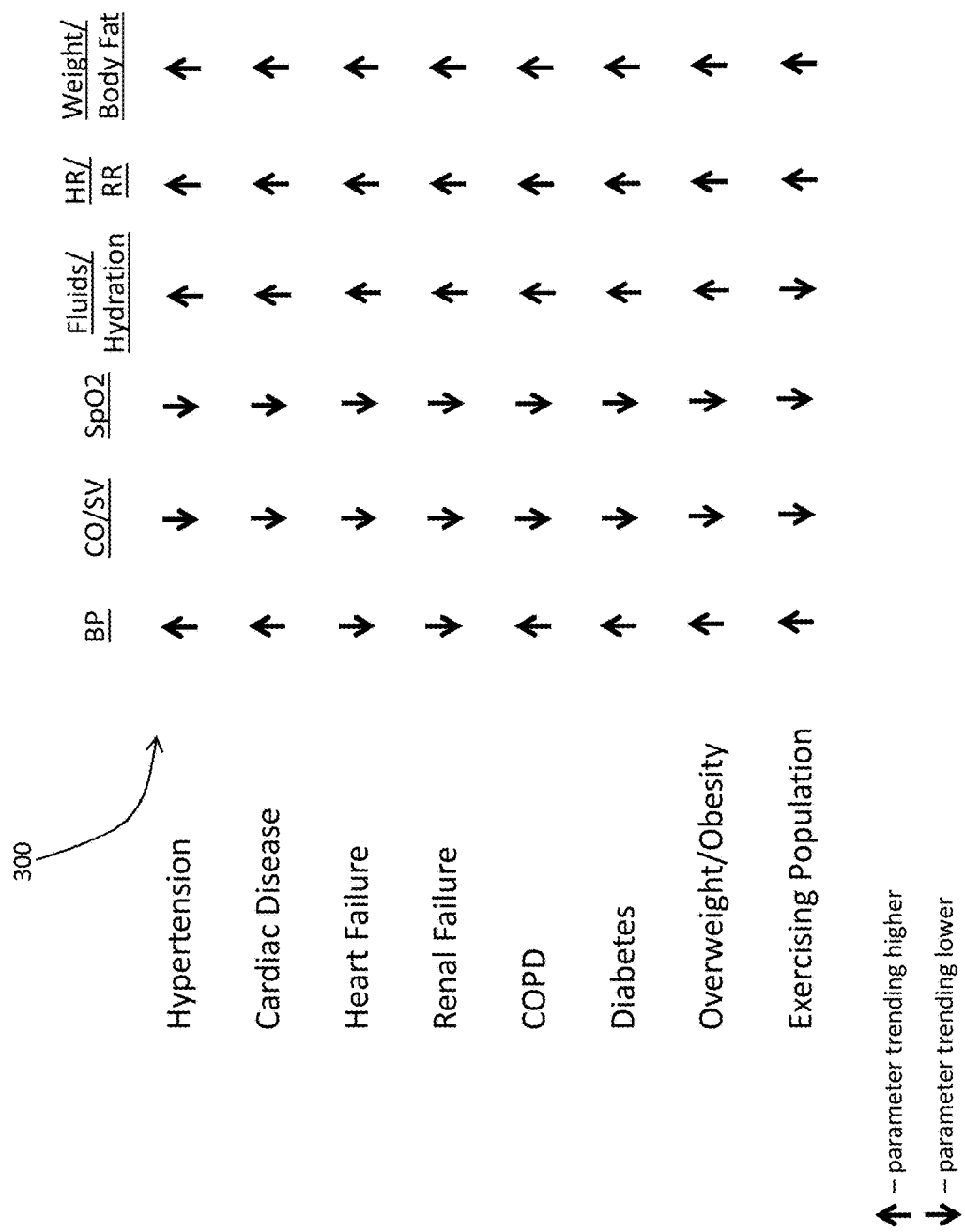
FIG. 15 is a table showing how parameters measured by the floormat and body-worn system trend with specific disease states and populations.

In general, the overarching purpose of the monitoring system featuring a floormat and body-worn sensor system according to the invention, as described above, is to make daily measurements of a wide range of physiological parameters that, in turn, can be analyzed to diagnose specific disease states, particularly measurements of BP and SV, not available on conventional weight scales or body worn sensors. It is often the time-dependent trends in the physiological parameters that provide the best indication of such disease states. At a simple level, for example, a patient's weight value of 200 pounds his limited clinical value by itself. However, a weight value that rapidly increases from 200 to 210 pounds over a period of a few days may indicate the onset of a disease, such as CHF. In general, it is a collection of trends in multiple physiological parameters that often serve as the best marker for the onset of disease states. In this regard, FIG. 15 shows, for example, a table 300 indicating how trends in different physiological parameters can be used to diagnose disease states such as hypertension, cardiac disease, heart failure, renal failure, chronic obstructive pulmonary disease (COPD), diabetes, and obesity. In addition, the table 300 indicates how such trends may show beneficial progress to a population actively involved in exercise.

Embodiments other than those described above are within the scope of the invention. For example, the mechanical configuration of the floormat can take many shapes. In one embodiment, the floormat has a mechanical configuration similar to that of a conventional weight scale. Here, it may feature a rigid base, four distinct feet, and a cross-sectional shape that is relatively square. In an alternative embodiment, the floormat may feature the mechanical configuration of a conventional yoga mat and would be made with a flexible material (e.g. foam or silicone rubber) that can be easily rolled. In that case, electronic components required to measure all of the above-mentioned parameters would be embedded in the flexible material and may connect through flexible electronics, e.g. a flex circuit made from a polymeric material such as Kapton. Or the floormat may feature a rigid base and a surrounding flexible portion that can be removed, washed, and customized for the patient. Other mechanical configurations are also possible, such as one that includes foot-worn enclosures, e.g. something resembling a slipper, sandal, or shoe. In that case, electronics would be embedded in the soles of the foot-worn enclosures, which would typically connect to each other with a wire or flexible circuit.

Likewise, the mechanical configuration of the body-worn sensor can take many shapes. The sensor, for example, can be shaped like a necklace as described above, but feature semi-rigid members that secure to each side of the patient's neck (in a manner similar to a conventional stethoscope). In a related embodiment the sensor is shaped like a decorative 'choker'. In still other embodiments, the sensor can be formed as a patch, and held in place by its adhesive electrodes.

In a preferred embodiment such as the one described above, neither the floormat nor body-worn sensor includes a display. Omission of a display reduces costs and complexity associated with manufacturing and simplifies the design of these devices. Additionally, most patients using the floormat and body-worn sensor will have a conventional mobile device, such as a smartphone or tablet, and such devices typically have high-resolution displays (e.g., those featuring organic LED or liquid crystals) that are driven by sophisticated operating systems, and such systems can easily display all the numerical and waveform information generated by the devices.

Alternatively, the floormat and/or body-worn sensor may include a simple display, e.g., one that displays basic waveform and numerical information. Here, the devices may include one or more colored LEDs that indicate its overall status, e.g., its battery power; whether or not a measurement is ready to start or is complete; and if an error was present during the measurement.

Sensors and electronics other than those described above can be used for both the floormat and body-worn sensor. For example, while a Wheatstone Bridge is a conventional circuit for measuring weight, this sensor can be replaced by something more suitable to the floormat's form factor, e.g., a thin, pressure-sensitive resistor such as that manufactured by Tekscan (www.tekscan.com). Likewise, the circuitry in the body-worn sensor described above for measuring BI, ECG, and PPG waveforms can be replaced by an alternative circuit that performs a similar function. Furthermore, wireless transmitters, e.g. the Bluetooth®, WiFi®, and cellular transmitters described above, can be replaced by other short- or long-range radios that perform essentially the same function.

Other sensors not described in detail above may be incorporated into the floormat and/or body-worn sensor. For example, the body-worn sensor may include an optical system similar to that described above. This may be used, for example, to measure SpO2 values and PPG waveforms from the chest. The PPG waveforms may then be used to calculate PAT and VTT and then used to measure blood pressure, as described above. In still other embodiments, either the floormat or body-worn sensor may include a spirometer or end-tidal CO2 sensor to measure respiration rate, expelled gasses, and respiratory effort. The devices component may also include a glucometer for measuring glucose levels in the patient's blood or an ultrasound sensor for taking simple, Doppler-type images from the patient. In other embodiments, the floormat may link to other conventional wearable devices, such as devices that track a patient's activity and/or HR during exercise or devices such as ambulatory blood pressure monitors.

The GUI operating on the mobile device may serve many different functions. As described above, its primary function is to display numerical and waveform information from the patient. Additionally, it may: i) display trends in these values; ii) indicate a particular disease state (such as those listed in the table shown in FIG. 15); iii) prompt the patient to step on the floormat; iv) link the floormat to a website involving social media or to a website viewable by family, friends, or a pre-approved clinician; v) provide guidance to the patient on managing their condition; vi) be used to enter biometric information that is not measurable by the floormat, such as the patient's age, height, race, or gender; vii) estimate and render the patient's physical age (based on parameters such as body-mass index and HR); viii) track the patient's performance vs. goals; ix) compare data measured from the patient to other data (e.g. in their age group) to promote competition; and x) show advertisements from relevant vendors. Other software-based applications are, of course, possible with the mobile device and its associated GUI.

In other embodiments, the system shown above can integrate with a 'patch' that directly adheres to a portion of a patient's body, as opposed to a 'necklace' that drapes around the patient's neck. The patch would be similar in form to the necklace's base, although it may take on other shapes and form factors. It would include most or all of the same sensors (e.g. sensors for measuring ECG, TBI, and PPG waveforms) and computing systems (e.g. microprocessors operating algorithms for processing these waveforms to determine parameters such as HR, HRV, RR, BP, SpO2, TEMP, CO, SV, fluids) as the base of the necklace. However unlike the system described above, the battery to power the patch would be located in or proximal to the base, as opposed to the strands in the case of the necklace. Also, in embodiments, the patch would include a mechanism such as a button or tab functioning as an on/off switch. Alternatively, the patch would power on when sensors therein (e.g. ECG or temperature sensors) detect that it is attached to a patient.

In typical embodiments, the patch includes a reusable electronics module (shaped, e.g., like the base of the necklace) that snaps into a disposable component that includes electrodes similar to those described above. The patch may also include openings for optical and temperature sensors as described above. In embodiments, for example, the disposable component can be a single disposable component that receives the reusable electronics module. In other embodiments, the reusable electronics module can include a reusable electrode (made, e.g., from a conductive fabric or elastomer), and the disposable component can be a simple adhesive component that adheres the reusable electrode to the patient.

In preferred embodiments the patch is worn on the chest, and thus includes both rigid and flexible circuitry, as described above. In other embodiments, the patch only includes rigid circuitry and is designed to fit on other portions of the patient's body that is more flat (e.g. the shoulder).

In embodiments, for example, the system described above can calibrate the patch or necklace for future use. For example, the floormat can determine a patient-specific relationship between transit time and blood pressure, along with initial values of SYS, DIA, and MAP. Collectively these parameters represent a cuff-based calibration for blood pressure, which can be used by the patch or necklace for cuffless measurements of blood pressure. In other embodiments, the floormat can measure a full-body impedance measurement and weight. These parameters can be wirelessly transmitted to the necklace or patch, where they are used with their impedance measurement to estimate full-body impedance (e.g. during a dialysis session). Additionally, during the dialysis session, the necklace or patch can use the values of full-body impedance and weight to estimate a progression towards the patient's dry weight.

These and other embodiments of the invention are deemed to be within the scope of the following claims.

What is claimed is:

1. A system for measuring a stroke volume value from a patient, comprising:
   a floormat system for measuring a stroke volume calibration, comprising:
      a weight-measuring system comprising at least one strain gauge;
      a processing system configured to receive a signal that comprises at least one of an output of the strain gauge and derived from the output of the strain gauge, and then process this to determine a stroke volume calibration; and a first wireless system configured to wirelessly transmit information representing the stroke volume calibration; and a body-worn sensor comprising:
an electrical impedance system comprising at least four electrodes, at least one of which is configured to inject an electrical current into the patient's body, and at least one of which is configured to measure a signal induced by the electrical current and representative of an impedance plethysmogram;

a second wireless system configured to receive information representing the stroke volume calibration; and a processing system in electrical contact with the electrical impedance system and the second wireless system, and configured to receive signals from the electrical impedance system and convert them into a set of impedance values, the processing system further configured to analyze the set of impedance values and the stroke volume calibration to determine the stroke volume value.

2. The system of claim 1, wherein the stroke volume calibration comprises a value representing the patient's weight.

3. The system of claim 2, wherein the processing system comprises computer code configured to analyze the set of impedance values and the stroke volume calibration to determine the stroke volume value.

4. The system of claim 3, wherein the computer code is configured to calculate a derivative of the set of impedance values to determine a $d\Delta Z(t)/dt$ waveform.

5. The system of claim 4, wherein the computer code is configured to determine a maximum value of the $d\Delta Z(t)/dt$ waveform.

6. The system of claim 5, wherein the computer code is configured to determine an area of a pulse in the $d\Delta Z(t)/dt$ waveform.

7. The system of claim 4, wherein the computer code is configured to estimate an ejection time from the $d\Delta Z(t)/dt$ waveform.

8. The system of claim 4, wherein the computer code is configured to estimate a baseline impedance ($Z_0$) from the set of impedance values.

9. The system of claim 8, wherein the computer code is configured to determine: i) a maximum value of the $d\Delta Z(t)/dt$ waveform ($(d\Delta Z(t)/dt)_{max}$); and ii) a left ventricular ejection time (LVET) from the $d\Delta Z(t)/dt$ waveform.

10. The system of claim 9, wherein the computer code is configured to determine stroke volume (SV) from the equation:

$$SV \sim \frac{(d\Delta Z(t)/dt)_{max}}{Z_o} \times LVET.$$

11. The system of claim 9, wherein the computer code is configured to determine stroke volume (SV) from the equation:

$$SV \sim \sqrt{\frac{(d\Delta Z(t)/dt)_{max}}{Z_o}} \times LVET.$$

12. The system of claim 4, wherein the computer code is configured to determine stroke volume (SV) from the equation:

$$SV = V_c \times \frac{(d\Delta Z(t)/dt)_{max}}{Z_o} \times LVET$$

where $V_c$ is a volume conductor calculated from the value of the patient's weight.

13. The system of claim 4, wherein the computer code is configured to determine stroke volume (SV) from the equation:

$$SV = V_c \times \sqrt{\frac{(d\Delta Z(t)/dt)_{max}}{Z_o}} \times LVET$$

where $V_c$ is a volume conductor calculated from the value of the patient's weight.

14. The system of claim 1, wherein the stroke volume calibration comprises a value representing the patient's body composition.

15. The system of claim 1, wherein the first wireless system comprises a transmitter based on Bluetooth® or 802.11.

16. The system of claim 1, wherein the second wireless system comprises a transmitter based on Bluetooth® or 802.11.

17. The system of claim 1, wherein the electrical impedance system comprises an electrical system that injects a current modulated at a frequency between 25-125 kHz.

18. The system of claim 1, wherein the electrical impedance system comprises an electrical system that comprises two electrodes that inject the electrical current into the patient.

19. The system of claim 18, wherein the electrical impedance system comprises an electrical system that comprises two electrodes, each configured to measure a signal induced by the electrical current.

* * * * *